US008183029B2

(12) United States Patent
Leung et al.

(10) Patent No.: US 8,183,029 B2
(45) Date of Patent: *May 22, 2012

(54) REPLICABLE EXPRESSION VECTOR FOR BACTERIAL EXPRESSION OF A MAMMALIAN POLYPEPTIDE

(75) Inventors: Woon-Lam Susan Leung, San Mateo, CA (US); James R. Swartz, Menlo Park, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/727,789

(22) Filed: Mar. 19, 2010

(65) Prior Publication Data

US 2010/0173389 A1     Jul. 8, 2010

Related U.S. Application Data

(63) Continuation of application No. 09/422,528, filed on Oct. 21, 1999, now Pat. No. 7,858,339.

(60) Provisional application No. 60/106,053, filed on Oct. 28, 1998.

(51) Int. Cl.
| | |
|---|---|
| C12P 21/06 | (2006.01) |
| C12N 9/00 | (2006.01) |
| C12N 9/24 | (2006.01) |
| C12N 9/26 | (2006.01) |
| C12N 1/20 | (2006.01) |
| C12N 15/00 | (2006.01) |
| C07H 21/04 | (2006.01) |

(52) U.S. Cl. .............. 435/252.33; 435/69.1; 435/183; 435/200; 435/201; 435/320.1; 536/23.2

(58) Field of Classification Search .............. None
See application file for complete search history.

(56) References Cited

U.S. PATENT DOCUMENTS

| | | | |
|---|---|---|---|
| 4,336,336 | A | 6/1982 | Silhavy et al. |
| 4,595,658 | A | 6/1986 | Zinder et al. |
| 4,637,980 | A | 1/1987 | Auerbach et al. |
| 5,169,772 | A | 12/1992 | Zimmerman et al. |
| 6,180,367 | B1 | 1/2001 | Leung et al. |
| 6,258,560 | B1 | 7/2001 | Leung et al. |

FOREIGN PATENT DOCUMENTS

| | | |
|---|---|---|
| EP | 155189 | 9/1985 |
| EP | 006694 | 1/1992 |
| JP | 61-257931 | 11/1986 |
| RU | 2043415 | 10/1995 |
| RU | 2071501 | 1/1997 |
| RU | 2071503 | 1/1997 |
| WO | WO 93/06217 | 4/1993 |
| WO | WO 93/24633 | 12/1993 |
| WO | WO 97/21829 | 6/1997 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Van Dien et al. Appl Environ Microbiol. May 1997;63(5):1689-95.*
Ames, et al., "Simple, rapid and quantitative release of periplasmic proteins by chloroform", Journal of Bacteriology, 160(3): 1181-1183, (1984).
Anderson, et al., "Defective transport and other phenotypes of a periplasmic "leaky" mutant of *Escherishia coli* K-12", Journal of Bacteriology, 140(2): 351-358, (1979).
Ariga, et al., "Release of thermophilic α-amylase from transformed *Escherichia coli* by addition of glycine", Journal of Fermentation and Bioengineering, 68(4): 243-246, (1989).
Asami, at al, "Synchronized disruption of *Escherichia coli* cells by T4 phage infection". Journal of Fermentation and Bioengineering, 83(6): 511-516, (1997).
Beacham, "Periplasmic enzymes in gram-negative bacteria", International Journal of Biochemistry, 10(11): 877-883, (1979).
"Blast Results A-1—A( )" GenBank.
"Blast Results B-1—B( )" Dayhoff.
Carter, et al., "High level *Escherichia coli* expression and production of a bivalent humanized antibody fragment", Bio/Technology, 10: 163-167, (1992).
Dabora, et al., "Intracellular lytic enzyme systems and their use for disruption of *Escherichia coli*", Advances in Biochemical Engineering/Biotechnology, vol. 43: 11-30, (1990).
Fahey, et al, "On the cysteine and cysteine content of proteins. Differences between intracellular and extracellular proteins", Journal of Molecular Evolution, 10(2): 155-160, (1977).
French, et al., "Production and release of recombinant periplasmic enzymes from *Escherichia coli* fermentations", Journal of Chemical Technology and Biotechnology, 54(3): 301, (1992).
French, et al., "Development of a simple method for the recovery of recombinant proteins from the *Escherichia coli* periplasm", Enzyme and Microcial Technology, 19: 332-338, (1996).
Halfman, et al., "Targeting of interleukin-2 to the periplasm of *Escherichia coli*", Journal of General Microbiology, 139(pt 10): 2465-2473, (1993).
Hart, et al., "Large scale, in situ isolation periplasmic IGF-I from *E. coli*", Bio/Technology 12: 1113-1117, (1994).
Hobot, et al., "Periplasmic gel: new concept resulting from the reinvestigation of bacterial cell envelope ultrastructure by new methods", Journal of Bacteriology, 160(1): 143-152, (1984).
Holowachuk, et al., "Biologically active recombinant rat granulocyte macrophage colony-stimulating factor produced in *Escherichia coli*", Protein Expression & Purification, 6(5): 588-596, (1995).
Joseph-Liauzun, et al., "Human recombinant interleukin-1β isolated from *Escherichia coli* by simple osmotic shock", Gene, 86(2): 291-295, (1990).

(Continued)

*Primary Examiner* — Christian Fronda
(74) *Attorney, Agent, or Firm* — Arnold & Porter LLP; Craig Svoboda; Ginger R. Dreger

(57) ABSTRACT

Refractile particles containing a heterologous polypeptide as an insoluble aggregate are recovered from bacterial periplasm. The process involves culturing bacterial cells so as to express nucleic acid encoding phage lysozyme and nucleic acid encoding the heterologous polypeptide under separate promoters, disrupting the cells mechanically to release the phage lysozyme so as to release refractile particles from the bacterial cellular matrix, and recovering the released refractile particles from the periplasm. Chloroform is not used in any step and the recovery step minimizes co-recovery of cellular debris with the released refractile particles.

11 Claims, 17 Drawing Sheets

OTHER PUBLICATIONS

Josslin, et al., "The lysis mechanism of phage T4: mutants affecting lysis", Virology, 40(3): 719-726, (1970).

Karam, et al., "Molecular Biollogy of Bacteriophage T4", American Society of Microbiology, pp. 398-399, (1994).

Lazzaroni, et al., "Genetic and biochemical characterization of periplasmic-leaky mutants of *Escherichia coli* K-12", Journal of Bacteriology, 145(3): 1351-1358, (1981).

Leung, et al., "Genetic manipulations to improve large-scale product recovery", Abstract papers of the American Chemical Society, 216 Meeting(Pt. 1): Biot014 (1998).

Lopes, et al., "Leakage of periplasmic enzymes by mutants of *Escherichia coli* and *Salmonella typhimurium*: isolation of "periplasmic leaky" mutants", Journal of Bacteriology, 109(2): 520-525, (1972).

"Lysozyme", Worthington Enzyme Manual, Worthington Biochemical Corporation, pp. 219-223, (1988).

Matthews, et al., "Relation between hen egg white lysozyme and bacteriophage T4 lysozyme: evolutionary implications", Journal of Molecular Biology, 147(4): 545-558, (1981).

Mukai, et al., "The mechanism of lysis in phage T4-infected cells", Virology, 33(3):398-404, (1967).

Naglak, et al., "Recovery of a foreign protein from the periplasm of *Escherichia coli* by shemical permeabilization", Enzyme & Microbial Technology, 12(8): 603-611, (1990).

Neu, et al., "The release of enzymes from *Escherichia coli* by osmotic shock and during the formation of spheroplasts", Journal of Biological Chemistry, 240(9): 3685-3692, (1965).

Neu, et al, "The release of ribonuclease into the medium when *Escherichia coli* cells are converted to spheroplasts", Journal of Biological Chemistry, 239(11): 3893-3900, (1964).

Nossal, et al., "The release of enzymes by osmotic shock from *Escherichia coli* in exponential phase", Journal of Biological Chemistry, 241(13): 3055-3062, (1966).

Pierce, et al.. "Expression and recovery of recombinant periplasmically secreted α amylase derived from *Streptomyces thermoviolaceus*", The 1995 ICheme Research Event/First European Conference, 2: 995-997, (1995).

Pluckthun, et al., "Antibodies from *Escherichia coli*", Nature, 347(6292): 497-498, (1990).

Pugsley, et al., "Export and secretion of proteins by bacteria", FEMS Microbiology Reviews, 32: 3-38, (1985).

Rockenbach, et al., "Secretion of active truncated CD4 into *Escherichia coli* periplasm", Applied Microbiology and Biotechnology, 35: 32-37. (1991).

Stabel, et al., "Periplasmic location of *Brucella abortus* Cu/Zn superoxide dismutase", Veterinary Microbiology, 38(4): 307-314, (1994).

Strauss, et al., "Chemical synthesis of a gene for human stefin A and its expression in *E. coli*", Biological Chemistry, 369: 1019-1030, (1988).

Swamy, et al., "Subcellular distribution of various proteases in *Escherichia coli*", Journal of Bacteriology, 149(3): 1027-1033, (1982).

Swartz, et al., "*E. coli* host modification for improved rDNA product quality and product recovery" (Abstract orally presented at the Separation Technology VII meeting entitled, "Separartion for clean production", sponsored by the Engineering Foundation held in Davos, Switzerland on Oct. 28, 1997).

Tanji, et al., "Controlled expression by lysis genes encoded in T4 phage for the gentle disruption of *Escherichia coli* cells", Journal of Fermentation and Bioengineering, 85(1): 74-78, (1998).

Tarragona, et al., "Production of mature bovine pancreatic ribonuclease in *Escherichia coli*", Gene, 118: 239-245, (1992).

Tsugita, et al., "Complete primary structure of phage lysozyme from *Escherichia coli* T4", Journal of Molecular Biology, 37(1): 201-212, (1968).

Tsugita, et al., "Purification of bacteriophage T4 lysozyme", Journal of Biological Chemistry, 243: 391-397, (1968).

Vasquez, et al., "An expression system for trypsin", Journal of cellular Biochemistry, 39(3): 365-376, (1989).

Villa-Komaroff, et al., "A bacterial clone synthesizing proinsulin", PNAS, 75(8): 3727-3731, (1978).

Witholt, et al., "How does lysozyme penetrate through the bacterial outer membrane?", Biochimica, et Biophysica Acta, 443(3): 534-544, (1976).

Zinder, et al, "Production of protoplasts of *Escherichia coli* lysozyme treatment", PNAS, 42: 586-590, (1956).

Leung, et al., Book of Abstracts, 216th ACS National Meeting, Boston, Aug. 23-27, 1998, BIOT-014. American Chemical Society.

Wick, et al., "Compartmentalization of defined epitopes expressed in *Escherichia coli* has only a minor influence on efficiency of phagocytic processing for presentation by class I and class II major histocompatibility complex molecules to T cells", Infection and Immunity, vol. 61, No. 11, pp. 4848-4856, (1993).

Balbas, et al., "A pBRINT family of plasmids for integration of cloned DNA into the *Escherichia coli* chromosome", Gene, 172, 65-69, (1996).

Van Dien, et al., "Manipulation of independent synthesis and degradation of polyphosphate in *Escherichia coli* for investigation of phosphate secretion from the cell", Applied and Environmental Microbiology, vol. 63, No. 5, pp. 1689-1695, (1997).

\* cited by examiner

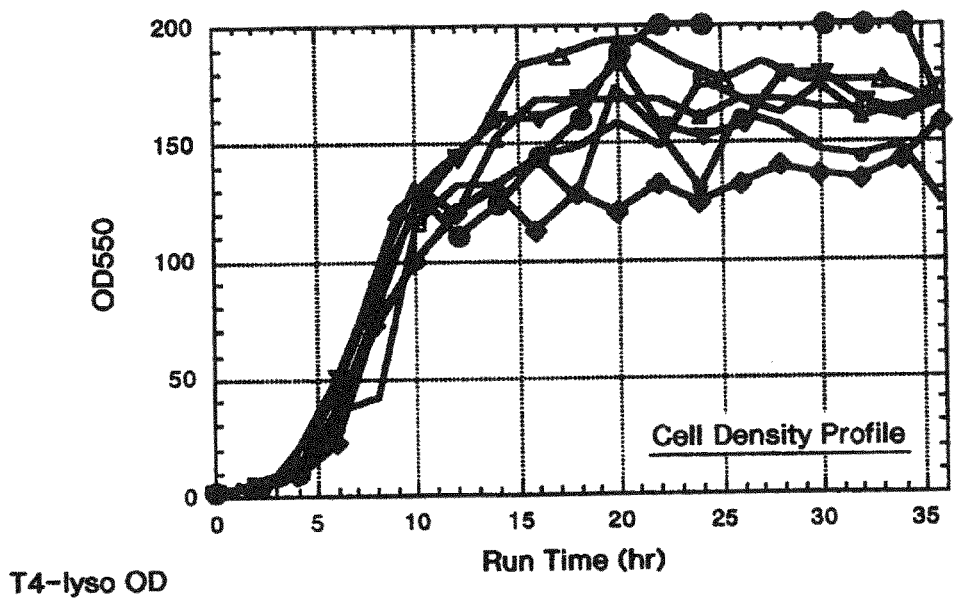

Effect of Arabinose Induction for T4-lysozyme Co-expression on Cell Density Profile

Run ID Key:

| Run # | Production Organism | Test Condition |
|---|---|---|
| SI1613 | 45F8/pLBIGF57 | Control organism, no arabinose induction |
| SI1609 | 45F8/pIGFLysAra | Minus arabinose induction control |
| SI1599 | 45F8/pIGFLysAra | 0.1% arabinose induction @ 32 hrs |
| SI1608 | 45F8/pIGFLysAra | 1% arabinose induction @ 36 hrs |
| SI1610 | 45F8/pIGFLysAra | 1% arabinose induction @ 32 hrs |
| SI1554 | 45F8/pIGFLysAra | 1% arabinose induction @ 32 hrs |
| SI1547 | 45F8/pIGFLysAra | 0.1% arabinose induction @ 24 hrs |

FIG. 6

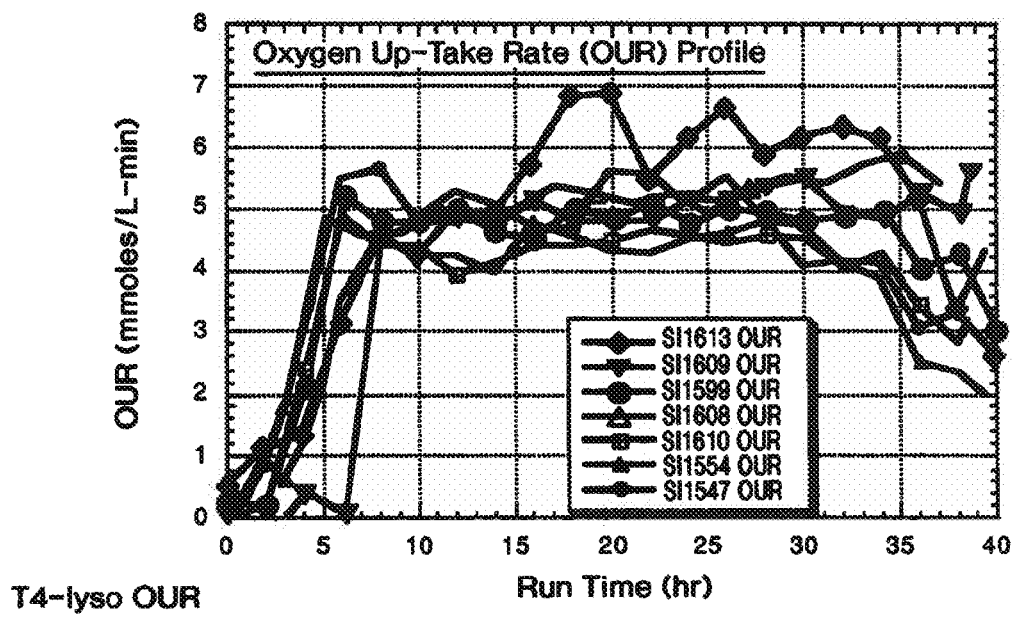

Effect of Arabinose Induction for T4-lysozyme Co-expression on Cellular Respiration

Run ID Key:

| Run # | Production Organism | Test Condition |
|---|---|---|
| SI1613 | 45F8/pLBIGF57 | Control organism, no arabinose induction |
| SI1609 | 45F8/pIGFLysAra | Minus arabinose induction control |
| SI1599 | 45F8/pIGFLysAra | 0.1% arabinose induction @ 32 hrs |
| SI1608 | 45F8/pIGFLysAra | 1% arabinose induction @ 36 hrs |
| SI1610 | 45F8/pIGFLysAra | 1% arabinose induction @ 32 hrs |
| SI1554 | 45F8/pIGFLysAra | 1% arabinose induction @ 32 hrs |
| SI1547 | 45F8/pIGFLysAra | 0.1% arabinose induction @ 24 hrs |

RP Recovery Process Evaluation
VEGF Broth Induced for T4-Lysozyme Co-expression

Gel Analysis of RP Recovered:

RP Recovery Process Evaluation
DNase Broth Induced for T4-Lysozyme Co-expression

REPLICABLE EXPRESSION VECTOR FOR BACTERIAL EXPRESSION OF A MAMMALIAN POLYPEPTIDE

RELATED APPLICATIONS

This application is a continuation application of non-provisional application Ser. No. 09/422,528, filed Oct. 21, 1999 now U.S. Pat. No. 7,858,339, filed under 37 CFR 1.53(b)(1), claiming priority under 35 USC 119(e) to provisional application No. 60/106,053, filed Oct. 28, 1998, the contents of which are incorporated herein by reference.

SEQUENCE LISTING

In accordance with 37 CFR 1.821(e), we hereby expressly incorporate herein by reference, in its entirety, the last-filed (filed Oct. 21, 1999) computer readable Sequence Listing, saved as "P1190R1 Seq Listing.txt", date of creation Oct. 21, 1999, size 8.00 KB (8,192 bytes), submitted in U.S. application Ser. No. 09/422,528, filed Oct. 21, 1999.

BACKGROUND OF THE INVENTION

1. Field of the Invention

This invention relates to a process for producing and recovering polypeptides from bacterial cells. More particularly, this invention relates to a process wherein recovery of insoluble recombinant polypeptides from bacterial periplasm is increased.

2. Description of Related Disclosures

*Escherichia coli* has been widely used for the production of heterologous proteins in the laboratory and industry. *E. coli* does not generally excrete proteins to the extracellular medium apart from colicins and hemolysin (Pugsley and Schwartz, *Microbiology,* 32: 3-38 (1985)). Heterologous proteins expressed by *E. coli* may accumulate as soluble product or insoluble aggregates. See FIG. 1 herein. They may be found intracellularly in the cytoplasm or be secreted into the periplasm if preceded by a signal sequence. How one proceeds initially in the recovery of the products greatly depends upon how and where the product accumulates. Generally, to isolate the proteins, the cells may be subjected to treatments for periplasmic extraction or be disintegrated to release trapped products that are otherwise inaccessible.

The secretion of recombinant proteins to the periplasmic space has numerous advantages over expression in the cytoplasm. The periplasmic space contains only 7 out of the 25 known cellular proteases (Swamy and Goldberg, *J. Bacteriol.,* 149: 1027-1033 (1982); French and Ward, *J. Chem. Tech. and Biol.,* 54 (3): 301 (1992)) and comprises only 4-8% of the total cell protein (Beacham, *Int. J. Biochem.,* 10: 877-883 (1979)). The mature secreted protein does not include N-formyl methionine and the oxidative environment of the periplasm facilitates correct disulfide bonding and protein folding (Fahey et al., *J. Mol. Evol.,* 10: 155-160 (1977)). Numerous heterologous proteins have been secreted to the periplasmic space of *E. coli.* Some have involved use of fusion proteins (VIIIa-Komaroff et al., *Proc. Natl. Acad. Sci. USA,* 75: 3727-3731 (1978); EP 6,694; and U.S. Pat. No. 4,336,336). Specific products prepared include antibody fragments (Pluckthun, *Nature,* 347: 497-498 (1990); WO 93/06217), ribonuclease A (Tarragona-Fiol et al., *Gene,* 118: 239-245 (1992)), HIV-1 receptor (Rochenbach et al., *Appl. Microbiol. Biotechnol.,* 35: 32-37 (1991)), trypsin (Vasquez et al., *J. Cell. Biochem.,* 39: 265-276 (1989)); human stefin A (Strauss et al., *Biol. Chem. Hoppe Syeler,* 369: 1019-1030 (1988)), xylanase (Bon-Joon et al., *J. Microb. and Tech.,* 6: 414-419 (1996)), rat GM-CSF (Holowachuk and Ruhoff, *Protein Exp. and Purification,* 6: 588-596 (1995)), and interleukin-2 (Halfmann et al., *J. Gen. Microbiol.,* 139: 2465-2473 (1993)).

The conventional isolation of heterologous polypeptide from gram-negative bacteria poses problems owing to the tough, rigid cell walls that surround these cells. The bacterial cell wall maintains the shape of the cell and protects the cytoplasm from osmotic pressures that may cause cell lysis; it performs these functions as a result of a highly cross-linked peptidoglycan (also known as murein) backbone that gives the wall its characteristic rigidity. A recent model described the space between the cytoplasmic and outer membranes as a continuous phase filled with an inner periplasmic polysaccharide gel that extends into an outer highly cross-linked peptidoglycan gel (Hobot et al., *J. Bact.,* 160: 143 (1984)). This peptidoglycan sacculus constitutes a barrier to the recovery of any heterologous polypeptide not excreted by the bacterium into the medium.

To release recombinant proteins from the *E. coli* periplasm, treatments involving chemicals such as chloroform (Ames et al., *J. Bacteriol.,* 160: 1181-1183 (1984)), guanidine-HCl, and Triton X-100 (Naglak and Wang, *Enzyme Microb. Technol.,* 12: 603-611 (1990)) have been used. However, these chemicals are not inert and may have detrimental effects on many recombinant protein products or subsequent purification procedures. Glycine treatment of *E. coli* cells, causing permeabilization of the outer membrane, has also been reported to release the periplasmic contents (Ariga et al., *J. Ferm. Bioenq.,* 68: 243-246 (1989)). These small-scale periplasmic release methods have been designed for specific systems. They do not translate easily and efficiently and are generally unsuitable as large-scale methods.

The most widely used methods of periplasmic release of recombinant protein are osmotic shock (Nosal and Heppel, *J. Biol. Chem.,* 241: 3055-3062 (1966); Neu and Heppel, *J. Biol. Chem.,* 240: 3685-3692 (1965)), hen eggwhite(HEW)-lysozyme/ethylenediamine tetraacetic acid (EDTA) treatment (Neu and Heppel, *J. Biol. Chem.,* 239: 3893-3900 (1964); Witholt et al., *Biochim. Biophys. Acta,* 443: 534-544 (1976); Pierce et al., *ICheme Research Event,* 2: 995-997 (1995)), and combined HEW-lysozyme/osmotic shock treatment (French et al., *Enzyme and Microb. Tech.,* 19: 332-338 (1996)). Typically, these procedures include an initial disruption in osmotically-stabilizing medium followed by selective release in non-stabilizing medium. The composition of these media (pH, protective agent) and the disruption methods used (chloroform, HEW-lysozyme, EDTA, sonication) vary among specific procedures reported. A variation on the HEW-lysozyme/EDTA treatment using a dipolar ionic detergent in place of EDTA is discussed by Stabel et al., *Veterinary Microbiol.,* 38: 307-314 (1994). For a general review of use of intracellular lytic enzyme systems to disrupt *E. coli,* see Dabora and Cooney in *Advances in Biochemical Engineering/Biotechnology,* Vol. 43, A. Fiechter, ed. (Springer-Verlag: Berlin, 1990), pp. 11-30.

HEW-lysozyme acts biochemically to hydrolyze the peptidoglycan backbone of the cell wall. The method was first developed by Zinder and Arndt, *Proc. Natl. Acad. Sci. USA,* 42: 586-590 (1956), who treated *E. coli* with egg albumin (which contains HEW-lysozyme) to produce rounded cellular spheres later known as spheroplasts. These structures retained some cell-wall components but had large surface areas in which the cytoplasmic membrane was exposed.

U.S. Pat. No. 5,169,772 discloses a method for purifying heparinase from bacteria comprising disrupting the envelope of the bacteria in an osmotically-stabilized medium, e.g., 20% sucrose solution using, e.g., EDTA, lysozyme, or an organic compound, releasing the non-heparinase-like proteins from the periplasmic space of the disrupted bacteria by exposing the bacteria to a low-ionic-strength buffer, and releasing the heparinase-like proteins by exposing the low-ionic-strength-washed bacteria to a buffered salt solution.

There are several disadvantages to the use of the HEW-lysozyme addition for isolating periplasmic proteins. The cells must be treated with EDTA, detergent, or high pH, all of which aid in weakening the cells. Also, the method is not suitable for lysis of large amounts of cells because the lysozyme addition is inefficient and there is difficulty in dispersing the enzyme throughout a large pellet of cells.

Many different modifications of these methods have been used on a wide range of expression systems with varying degrees of success (Joseph-Liazun et al., *Gene,* 86: 291-295 (1990); Carter et al., *Bio/Technology,* 10: 163-167 (1992)). Although these methods have worked on a laboratory scale, they involve too many steps for an efficient large-scale recovery process.

Efforts to induce recombinant cell culture to produce lysozyme have been reported. EP 155,189 discloses a means for inducing a recombinant cell culture to produce lysozymes, which would ordinarily be expected to kill such host cells by means of destroying or lysing the cell wall structure. Russian Pat. Nos. 2043415, 2071503, and 2071501 disclose plasmids and corresponding strains for producing recombinant proteins and purifying water-insoluble protein agglomerates involving the lysozyme gene. Specifically, the use of an operon consisting of the lysozyme gene and a gene that codes for recombinant protein enables concurrent synthesis of the recombinant protein and a lysozyme that breaks the polysaccharide membrane of *E. coli.*

U.S. Pat. No. 4,595,658 discloses a method for facilitating externalization of proteins transported to the periplasmic space of *E. coli.* This method allows selective isolation of proteins that locate in the periplasm without the need for lysozyme treatment, mechanical grinding, or osmotic shock treatment of cells. U.S. Pat. No. 4,637,980 discloses producing a bacterial product by transforming a temperature-sensitive lysogen with a DNA molecule that codes, directly or indirectly, for the product, culturing the transformant under permissive conditions to express the gene product intracellularly, and externalizing the product by raising the temperature to induce phage-encoded functions. JP 61-257931 published Nov. 15, 1986 discloses a method for recovering IL-2 using HEW-lysozyme. Asami et al., *J. Ferment. and Bioeng.,* 83: 511-516 (1997) discloses synchronized disruption of *E. coli* cells by T4 phage infection, and Tanji et al., *J. Ferment. and Bioeng.,* 85: 74-78 (1998) discloses controlled expression of lysis genes encoded in T4 phage for the gentle disruption of *E. coli* cells.

The development of an enzymatic release method to recover recombinant periplasmic proteins suitable for large-scale use is reported by French et al., *Enzyme and Microbial Technology,* 19: 332-338 (1996). This method involves resuspension of the cells in a fractionation buffer followed by recovery of the periplasmic fraction, where osmotic shock immediately follows lysozyme treatment. The effects of overexpression of the recombinant protein, *S. thermoviolaceus* α-amylase, and the growth phase of the host organism on the recovery are also discussed.

Further, *E. coli* mutants that leak various periplasmic enzymes have been isolated. For example, Lopes et al., *J. Bacteriol.,* 109(2): 520-525 (1972) treated *E. coli* cells with a mutagen such as nitrosoguanidine, and mutants excreting periplasmic enzymes were selected by enzyme assay systems. Such mutants included those leaking ribonuclease I, endonuclease I, and alkaline phosphatase. It is believed that these mutants are deficient in some component of the outer bacterial membrane leading to an increase in the cells' permeability. In addition, several excreted periplasmic proteins have been separated from the culture medium by antibody precipitation or SDS-polyacrylamide gel electrophoresis in order to characterize these "periplasmic leaky" mutants. See, for example, Anderson et al., *J. Bacteriol.* 140(2): 351-358 (1979) and Lazzaroni and Portalier, *J. Bacteriol.* 145 (3): 1351-1358 (1981).

In a 10-kiloliter-scale process for recovery of IGF-I polypeptide (Hart et al., *Bio/Technology,* 12: 1113 (1994)), the authors attempted the typical isolation procedure involving a mechanical cell breakage step followed by a centrifugation step to recover the solids. The results were disappointing in that almost 40% of the total product was lost to the supernatant after three passes through the Gaulin homogenizer. Hart et al., *Bio/Technoloqy* 12: 1113 (1994). See FIG. 2 herein. Product recovery was not significantly improved even when the classical techniques of EDTA and HEW-lysozyme additions were employed.

While HEW-lysozyme is the only practical commercial lysozyme for large-scale processes, lysozyme is expressed by bacteriophages upon infection of host cells. Lysis of *E. coli,* a natural host for bacteriophages, for example the T4 phages, requires the action of two gene products: e and t. Gene e encodes a lysozyme (called T4-lysozyme for the T4 phage) that has been identified as a muramidase (Tsugita and Inouye, *J. Biol. Chem.,* 243: 391 (1968)), while gene t seems to be required for lysis, but does not appear to have lysozyme activity. Gene t is required for the cessation of cellular metabolism that occurs during lysis (Mukai et al., *Vir.,* 33: 398 (1967)) and is believed to degrade or alter the cytoplasmic membrane, thus allowing gene product e to reach the periplasm and gain access to the cell wall (Josslin, *Vir.,* 40: 719 (1970)). Phage are formed by gene t-mutants, but lysis of the *E. coli* host does not occur except by addition of chloroform (Josslin, supra). Wild-type T4-lysozyme activity is first detected about eight minutes after T4 infection at 37° C., and it increases through the rest of the infection, even if lysis inhibition is induced. In the absence of secondary adsorption, cells infected by gene e mutants shut down progeny production and metabolism at the normal time, but do not lyse (*Molecular Genetics of Bacteriophage T4*, J. D. Karam, ed. in chief (American Society for Microbiology, Washington D.C., ASM Press, 1994), p. 398).

Recovery of insoluble IGF-I using T4-lysozyme was disclosed on Oct. 28, 1997 at the "Separation Technology VII meeting entitled 'Separations for Clean Production'" in Davos, Switzerland, sponsored by the Engineering Foundation.

For controlling cost of goods and minimizing process time, there is a continuing need for increasing the total recovery of insoluble heterologous polypeptides contained in refractile particles from the periplasmic space of prokaryotes. Further, there is a need for culturing of *E. coli* cells to high cell densities as an important factor for achieving efficient recombinant heterologous polypeptide production.

SUMMARY OF THE INVENTION

Accordingly, the present invention provides a process for recovering refractile particles containing a heterologous polypeptide from bacterial periplasm in which the polypeptide is insoluble comprising:

(a) culturing bacterial cells, which cells comprise nucleic acid encoding phage lysozyme, nucleic acid encoding the heterologous polypeptide, a signal sequence for secretion of the heterologous polypeptide, and separate promoters for each of the nucleic acid encoding the phage lysozyme and the nucleic acid encoding the heterologous polypeptide, wherein the promoter for the heterologous polypeptide is inducible and the promoter for the phage lysozyme is either a promoter with low basal expression or an inducible promoter, wherein in the absence of induction the promoter for the phage lysozyme is a promoter with low basal expression, the culturing being under conditions whereby when an inducer is added, expression of the nucleic acid encoding the phage lysozyme is induced after about 50% or more of the heterologous polypeptide has accumulated, and under conditions whereby the heterologous polypeptide is secreted into the periplasm of the bacteria as an aggregate and the phage lysozyme accumulates in a cytoplasmic compartment;

(b) disrupting the cells mechanically to release the phage lysozyme so as to release refractile particles from cellular matrix; and (c) recovering the released refractile particles from the periplasm, whereby chloroform is not used in any step of the process, and wherein the recovery step minimizes co-recovery of cellular debris with the released refractile particles.

It was found in cell recovery that mechanical breakage by itself is not sufficient for efficient release of the insoluble polypeptide in aggregate form such as refractile particles and that HEW-lysozyme does not work well. Coordinated expression of nucleic acid encoding phage lysozyme with nucleic acid encoding the polypeptide of interest provides a highly effective method for releasing insoluble refractile particles from the entanglement with the peptidoglycan layer. When the phage lysozyme gene is cloned behind a tightly-controlled promoter, for example, the pBAD promoter (also referred to as the ara promoter), cytoplasmic accumulation of phage lysozyme may be induced by the addition of an inducer (such as arabinose) at an appropriate time near the end of fermentation. By placing the nucleic acid expression of heterologous polypeptide and phage lysozyme under separate promoter control, one can independently regulate their production during fermentation. Without a signal sequence, the accumulated phage lysozyme is tightly locked up in the cytoplasmic compartment. Upon mechanical disruption of the cells, phage lysozyme is released to degrade the peptidoglycan layer. Furthermore, the optimal pH for T4-phage-lysozyme activity, which is a preferred embodiment, is about 7.3, which is about the neutral pH of most typical harvest broths.

The induction of the gene encoding the bacteriophage lysozyme after expression of the nucleic acid encoding the heterologous polypeptide results in a significant increase in the amount of insoluble heterologous polypeptide recovered from the periplasm of bacteria after mechanical cell disruption. The phage lysozyme is trapped in the cytoplasmic compartment during fermentation until release by such disruption. Besides product yield, the success of a recovery process is judged by the ease of operation, the process flow, the turn-around time, as well as the operation cost. The present invention alleviates several if not all these bottlenecks encountered in the large-scale recovery process.

The process herein also allows use of phage lysozyme at high cell density and increased scale. At high density, even partial leakiness of expression could have disastrous results. Further, it would not be expected that induction at the end of a long fermentation process and after substantial product accumulation would produce enough of the phage lysozyme to be effective. The present process does not pose problems at high cell densities such as increased viscosity and excessive foaming during the fermentation process. The examples herein demonstrate that the process of this invention enables the attainment of high cell density, effective induction and action of the system, and the processing of lysates derived from high-density cultures. Additionally, at least certain embodiments of the process herein require less mechanical disruption of the cells, leading to less large-scale processing time than with conventional processing.

BRIEF DESCRIPTION OF THE DRAWINGS

FIG. 6 shows the time course of optical density for seven IGF-I fermentation experiments entitled SI1613 (solid diamonds), SI1609 (downward solid triangles), SI1599 (solid large circles), SI1608 (open triangles), SI1610 (checked squares), SI1554 (upward solid triangles), and SI1547 (solid small squares). The experiment identification key is:

| Experiment # | Production Organism | Test Condition |
| --- | --- | --- |
| SI1613 | 45F8/pLBIGF57 | Control organism, no arabinose induction |
| SI1609 | 45F8/pIGFLysAra | Minus arabinose induction control |
| SI1599 | 45F8/pIGFLysAra | 0.1% arabinose induction at 32 hrs |
| SI1608 | 45F8/pIGFLysAra | 1% arabinose induction at 36 hrs |
| SI1610 | 45F8/pIGFLysAra | 1% arabinose induction at 32 hrs |
| SI1554 | 45F8/pIGFLysAra | 1% arabinose induction at 32 hrs |
| SI1547 | 45F8/pIGFLysAra | 0.1% arabinose induction at 24 hrs |

FIG. 7 shows the time course of oxygen uptake rate for the seven fermentation experiments described for FIG. 6.

Figure 8:
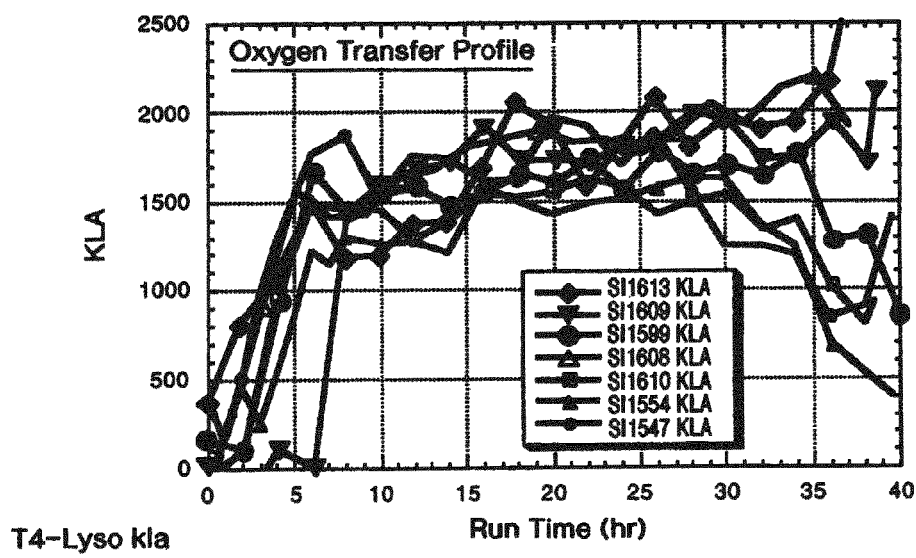

FIG. 8 shows the time course of oxygen transfer profile (KLA) for the seven fermentation experiments described for FIG. 6.

Figure 9:
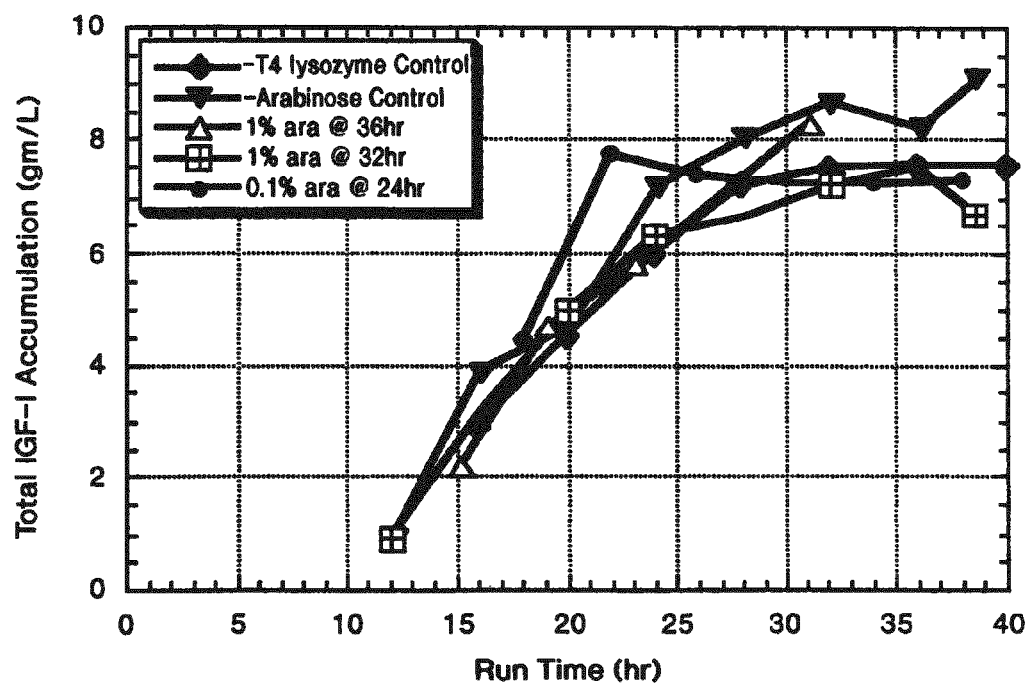

FIG. 9 shows the time course of IGF-I polypeptide accumulation for five fermentation experiments described for FIG. 6, i.e., -T4-lysozyme control (diamonds), -arabinose control (downward solid triangles), 1% ara at 36 hours (upward open triangles), 1% ara at 32 hours (quartered squares), and 0.1% ara at 24 hours (circles).

Figure 10:
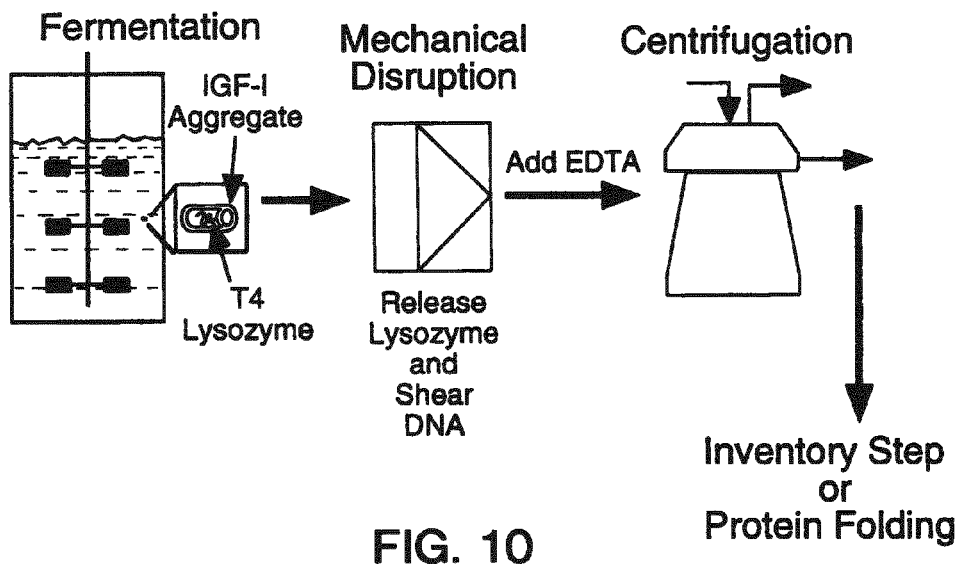

FIG. 10 shows the total schematic for the steps of this invention for producing IGF-I from culturing by use of induction of T4-lysozyme nucleic acid expression to isolation of IGF-I aggregates involving mechanical disruption and centrifugation.

Figure 11A:
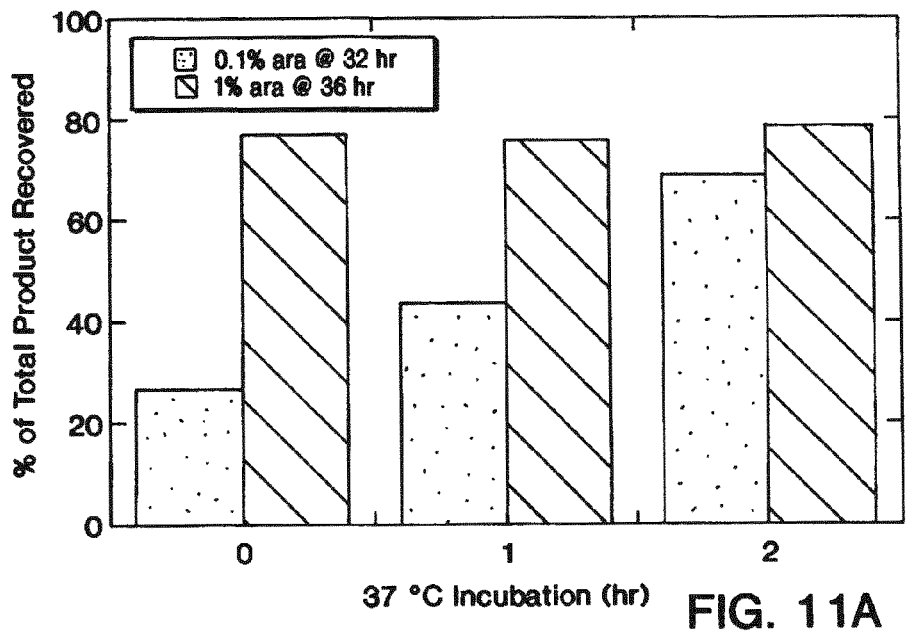
Figure 11B:
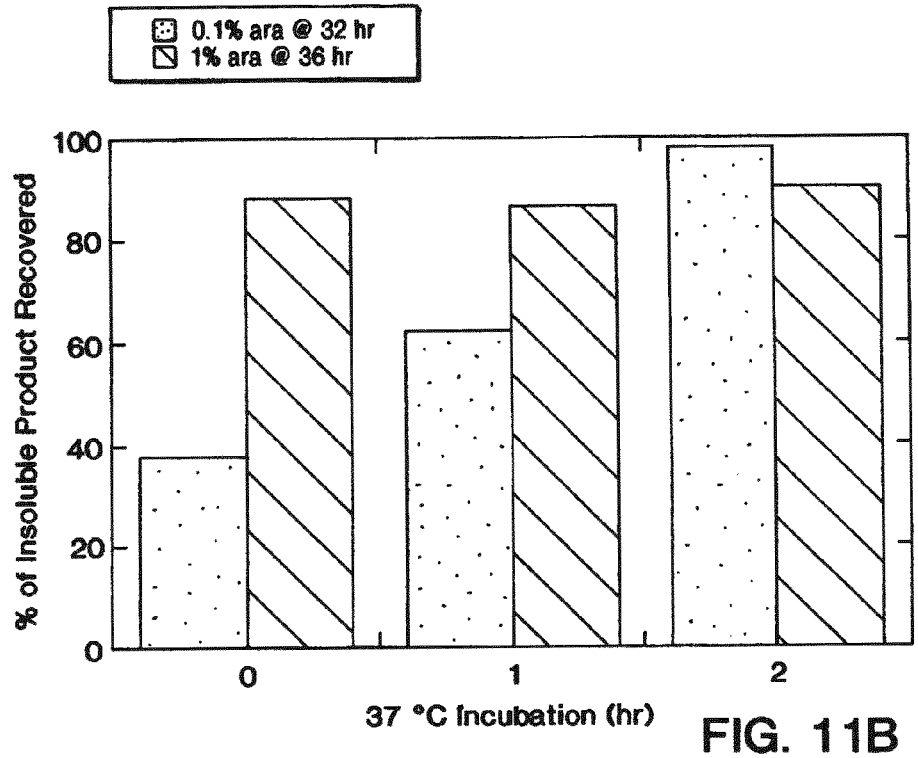

FIGS. 11A and 11B respectively show percent total IGF-I product recovered and percent insoluble product recovered when 0.1% arabinose at 32 hours (dark bars), or 1% arabinose at 36 hours (stippled bars) is used for 0, 1, and 2 hours of incubation at 37° C. The product is recovered by centrifugation at 5000 rpm×30 minutes in a SORVAL™ centrifuge using a GSA rotor.

Figure 12:
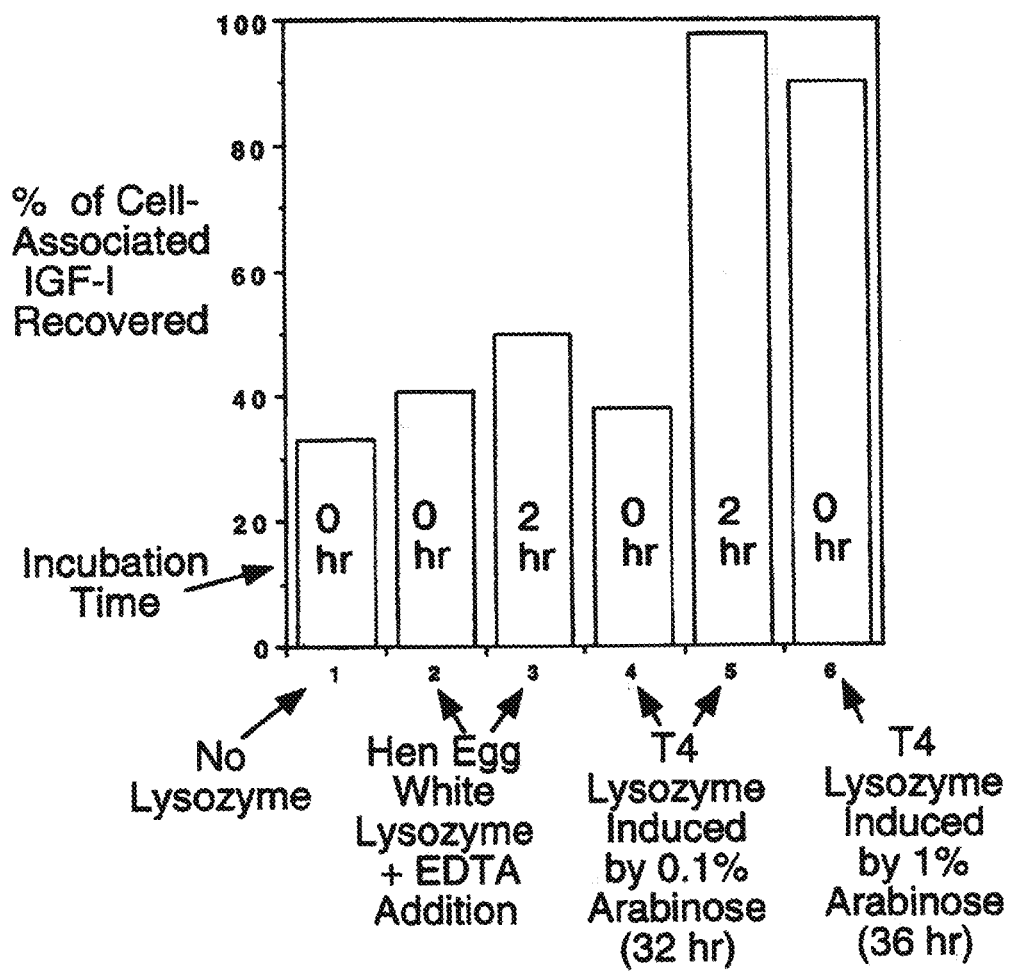

FIG. 12 shows the percent of cell-associated IGF-I recovered for 0 or 2 hours of incubation for (1) no lysozyme, (2 and 3) HEW-lysozyme+EDTA addition, (4 and 5) T4-lysozyme induced by 0.1% arabinose (32 hr), and (6) T4-lysozyme induced by 1% arabinose (36 hr).

Figure 13:
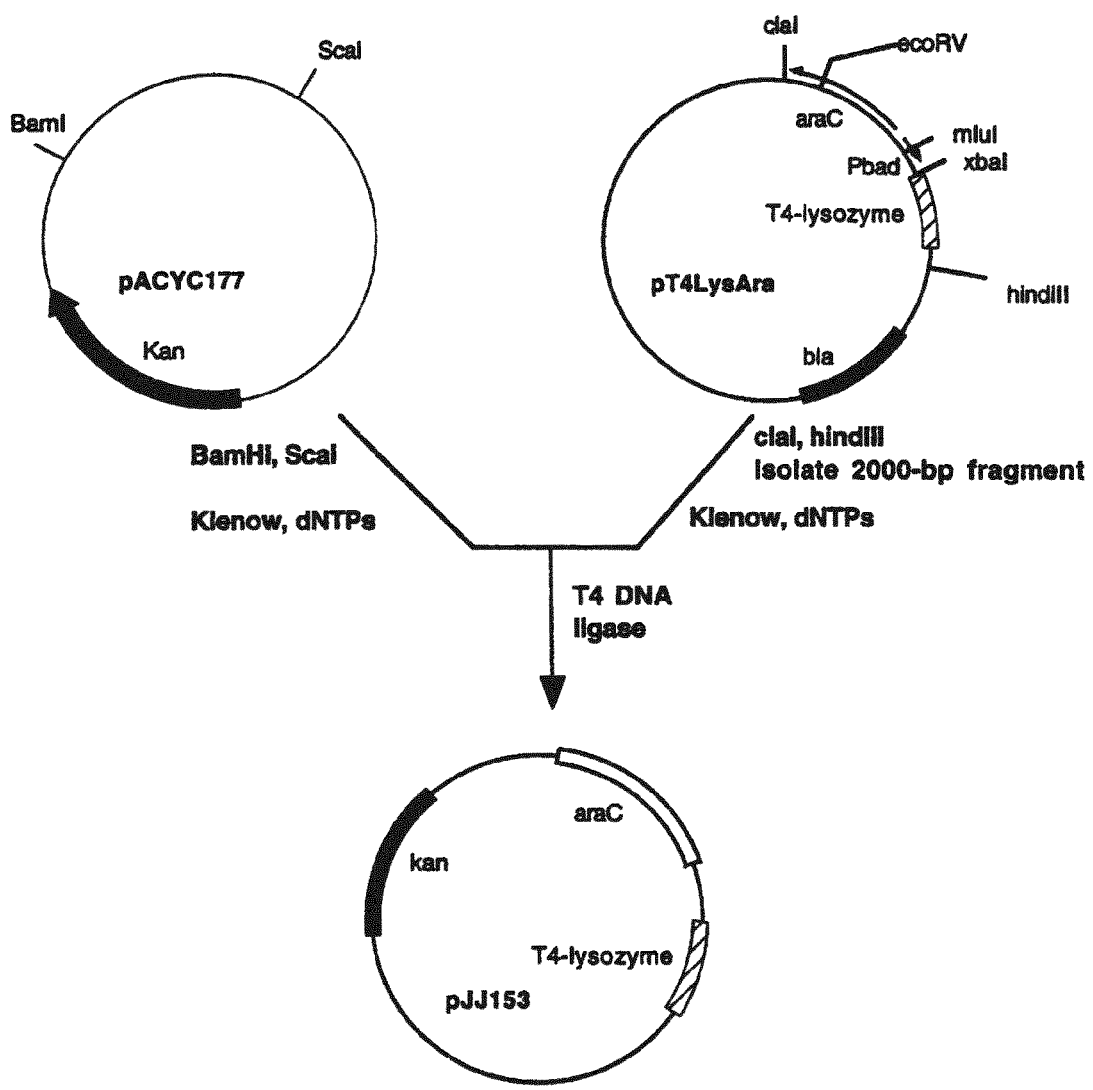

FIG. 13 shows the plasmid construction of pJJ153, which is used to express T4-lysozyme-encoding nucleic acid from a plasmid separate from that used for DNase (pLS20) or VEGF (pVEGF171) expression, where pJJ153 is prepared from pACYC177 and pT4LysAra.

Figure 14:
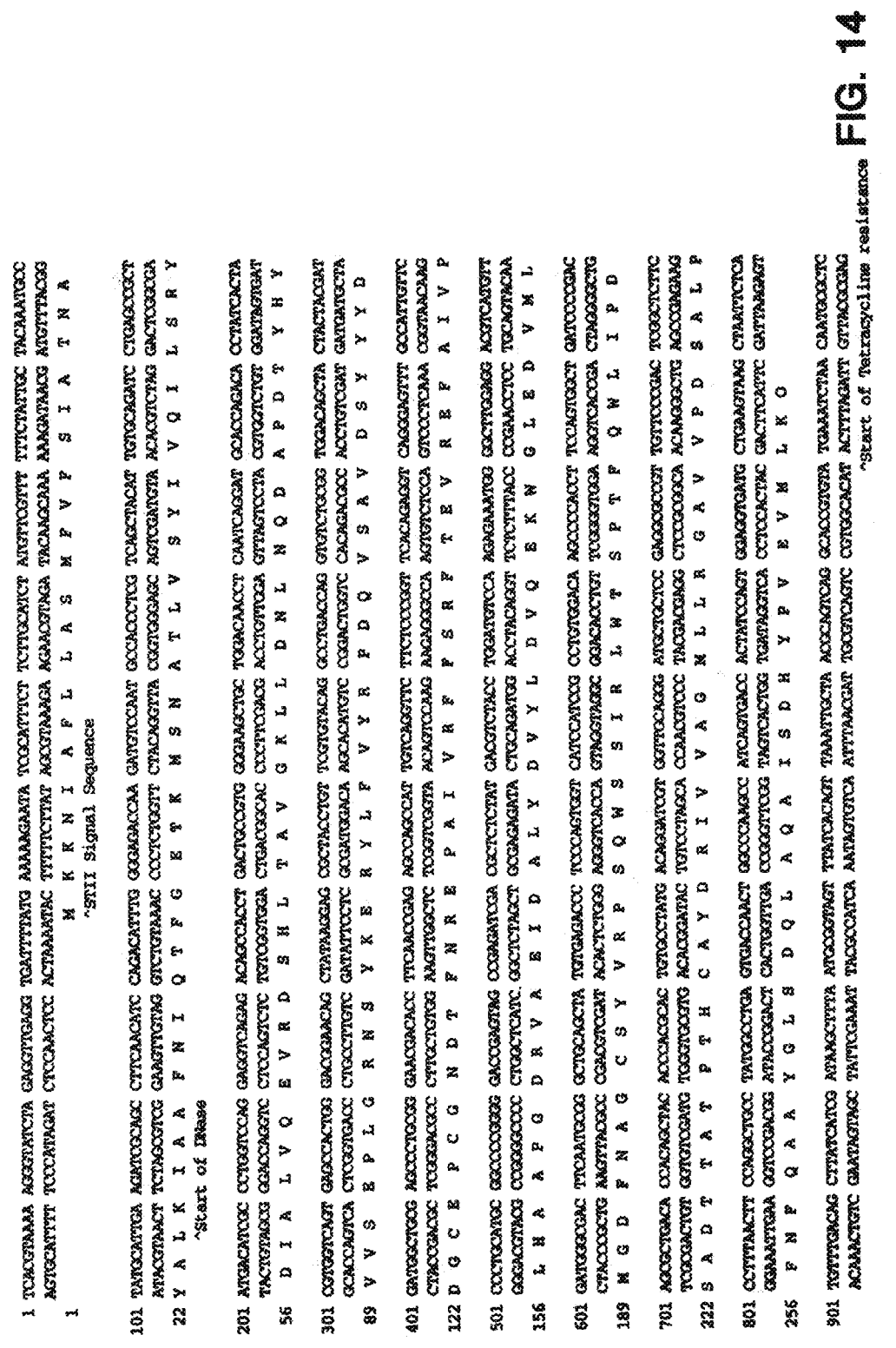

FIG. 14 discloses the forward and complementary nucleotide sequences (SEQ ID NOS:1 and 2, respectively) and the amino acid sequence (SEQ ID NO:3) for the STII signal sequence and DNase used for construction of pLS20.

Figure 15:
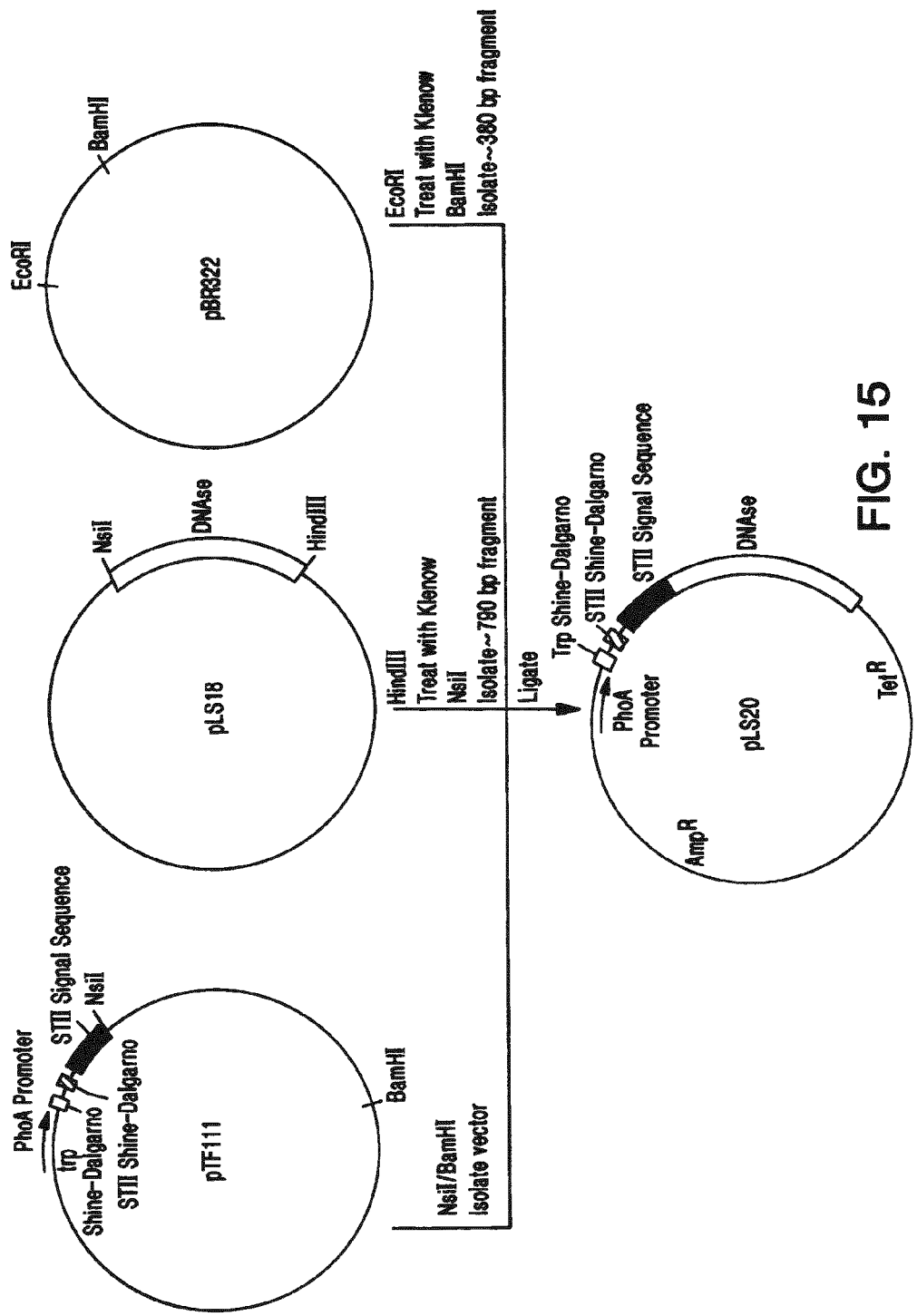

FIG. 15 discloses the plasmid construction of pLS20, a DNase expression vector, from pTF111, pLS18, and pBR322.

Figure 16:
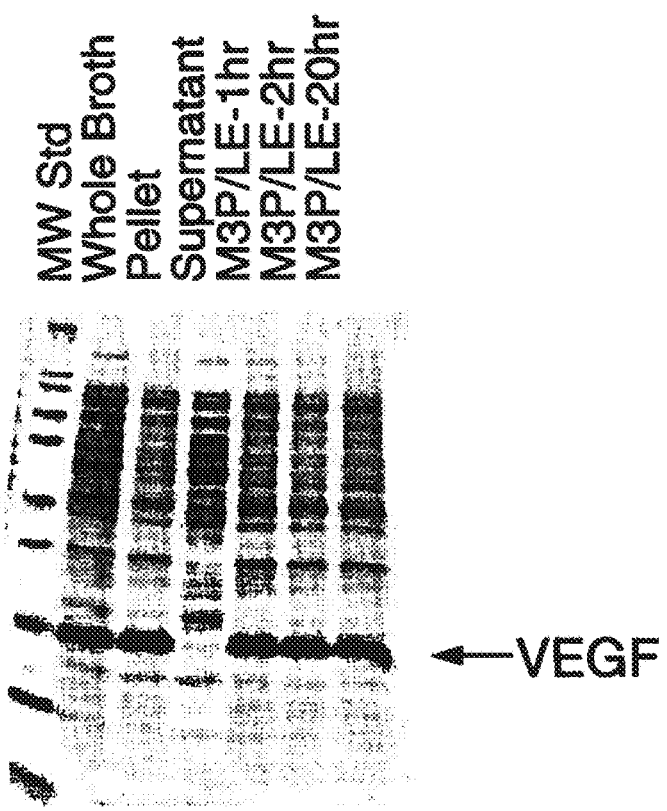

FIG. 16 shows the gel electrophoresis results in 10-20% TRICINE™ pre-cast gels (Novex) of VEGF broth induced for T4-lysozyme co-expression, where the left-most lane is molecular weight standards, the next lane is whole broth, the third lane is pellet passed through the MICROFLUIDIZER® mechanical disruption device (Microfluidics, Inc., Newton, Mass.), the fourth lane is supernatant, the fifth lane is the resuspended pellet from broth after three passes through the MICROFLUIDIZER® device (M3P) plus 5 mM final concentration EDTA (LE) at 37° C. for one hour, the sixth lane is M3P plus LE at 37° C. for two hours, and the seventh (right-most) lane is M3P plus LE at 37° C. for two hours with room-temperature incubation for 18 hours, for a total of 20 hours.

Figure 17:
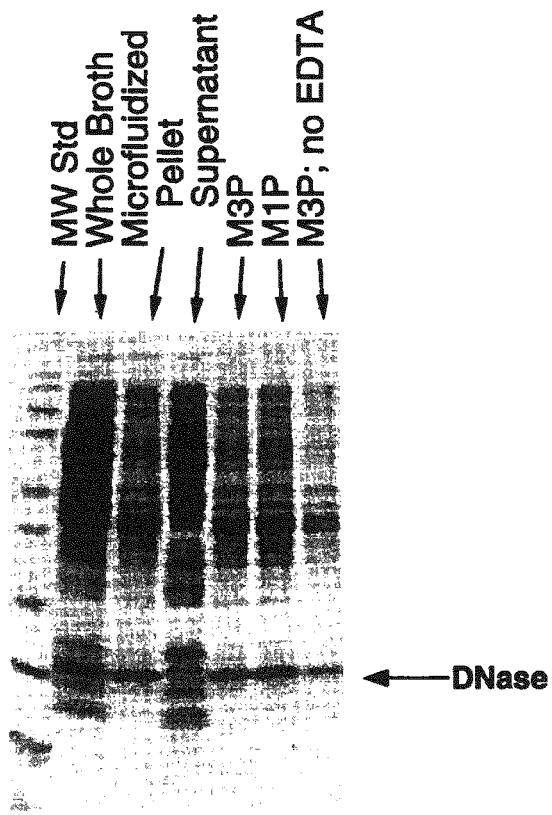

FIG. 17 shows the 10-20% TRICINE™ gel electrophoresis results of DNase broth induced for T4-lysozyme co-expression, where the left-most lane is molecular weight standards, the next lane is whole broth, the third lane is pellet passed through the MICROFLUIDIZER® device, the fourth lane is supernatant, the fifth lane is the resuspended pellet from broth after three passes through the MICROFLUIDIZER® device (M3P) plus 5 mM final concentration EDTA at 37° C. for two hours, the sixth lane is the resuspended pellet from broth after one pass through the MICROFLUIDIZER® device (M1P) plus 5 mM final concentration EDTA at 37° C. for two hours, and the seventh (right-most) lane is M3P with no EDTA.

DETAILED DESCRIPTION OF THE PREFERRED EMBODIMENTS

A. Definitions

As used herein, "phage lysozyme" refers to a cytoplasmic enzyme that facilitates lysis of phage-infected bacterial cells, thereby releasing replicated phage particles. The lysozyme may be from any bacteriophage source, including T7, T4, lambda, and mu bacteriophages. The preferred such lysozyme herein is T4-lysozyme.

As used herein, "T4-lysozyme", or "E protein", refers to a cytoplasmic muramidase that facilitates lysis of T4 phage-infected bacterial cells, thereby releasing replicated phage particles (Tsugita and Inouye, *J. Mol. Biol.* 37: 201-12 (1968); Tsugita and Inouye, *J. Biol. Chem.* 243: 391-97 (1968)). It is encoded by gene e of T4 bacteriophage and hydrolyzes bonds between N-acetylglucosamine and N-acetylmuramic acid residues in the rigid peptidoglycan layer of the *E. coli* cell envelope. The enzyme is a single polypeptide chain of a molecular weight of 18.3 kd. It is approximately 250-fold more active than HEW-lysozyme against bacterial peptidoglycan (Matthews et al., *J. Mol. Biol.*, 147: 545-558 (1981)). The optimal pH for T4-lysozyme enzyme activity is 7.3, versus 9 for HEW-lysozyme. (*The Worthington Manual*; pp 219-221).

As used herein, the phrase "agent that disrupts the outer cell wall" of bacteria refers to a molecule that increases permeability of the outer cell wall of bacteria, such as chelating agents, e.g., EDTA, and zwitterions.

As used herein, the term "bacteria" refers to any bacterium that produces proteins that are transported to the periplasmic space. The term "non-temperature-sensitive bacteria" refers to any bacterium that is not significantly sensitive to temperature changes. Generally, the bacteria, whether gram positive or gram negative, has lysozyme-encoding gene expression under control so that the gene is only expressed near the end of the fermentation, a preferred embodiment, or expressed at a low level during fermentation. Also, preferably the bacteria do not contain a temperature-sensitive phage repressor gene. Hence, the preferred non-temperature-sensitive bacteria herein are distinguished from bacteria containing defective temperature-sensitive lysogens such as lambda prophage that lack genes necessary for replication or structural protein assembly so that functional phage cannot be produced. The most preferred bacteria herein are gram-negative bacteria and/or bacteria that are non-temperature sensitive.

As used herein, "a time sufficient to release the polypeptide contained in the periplasm" refers to an amount of time sufficient to allow the lysozyme to digest the peptidoglycan to a sufficient degree to release the periplasmic aggregate or polypeptide.

As used herein, "signal sequence" or "signal polypeptide" refers to a peptide that can be used to secrete the heterologous polypeptide into the periplasm of the bacteria. The signal for the heterologous polypeptide may be homologous to the bacteria, or they may be heterologous, including signals native to the polypeptide being produced in the bacteria.

As used herein, "inducible" promoters are promoters that direct transcription at an increased or decreased rate upon binding of a transcription factor.

As used herein, a "promoter with low basal expression" or a "low-basal-level-expression promoter" is a promoter that is slightly leaky, i.e., it provides a sufficiently low basal expression level so as not to affect cell growth or product accumulation and provides a sufficiently low level of promotion not to result in premature cell lysis.

"Transcription factors" as used herein include any factors that can bind to a regulatory or control region of a promoter and thereby effect transcription. The synthesis or the promoter-binding ability of a transcription factor within the host cell can be controlled by exposing the host to an "inducer" or removing a "repressor" from the host cell medium. Accordingly, to regulate expression of an inducible promoter, an inducer is added or a repressor removed from the growth medium of the host cell.

As used herein, the phrase "induce expression" means to increase the amount of transcription from specific genes by exposure of the cells containing such genes to an effector or inducer.

An "inducer" is a chemical or physical agent which, when given to a population of cells, will increase the amount of transcription from specific genes. These are usually small molecules whose effects are specific to particular operons or groups of genes, and can include sugars, alcohol, metal ions, hormones, heat, cold, and the like. For example, isopropy-lthio-β-galactoside (IPTG) and lactose are inducers of the tacII promoter, and L-arabinose is a suitable inducer of the arabinose promoter.

A "repressor" is a factor that directly or indirectly leads to cessation of promoter action or decreases promoter action. One example of a repressor is phosphate. As the repressor phosphate is depleted from the medium, the alkaline phosphatase (AP) promoter is induced.

As used herein, "polypeptide" or "polypeptide of interest" refers generally to peptides and proteins having more than about ten amino acids. Those that are secreted to the periplasm of the bacteria may associate with the bacterial cell wall. The recovery of these polypeptides from bacterial periplasm improves with the co-expression of phage lysozyme. The polypeptides are "heterologous," i.e., foreign to the host cell being utilized, such as a human protein produced by E. coli. The polypeptide is produced as an insoluble aggregate in the periplasmic space.

Examples of mammalian polypeptides include molecules such as, e.g., renin, a growth hormone, including human growth hormone; bovine growth hormone; growth hormone releasing factor; parathyroid hormone; thyroid stimulating hormone; lipoproteins; α1-antitrypsin; insulin A-chain; insulin B-chain; proinsulin; thrombopoietin; follicle stimulating hormone; calcitonin; luteinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as brain-derived neurotrophic factor (BDNF), neurotrophin-3, -4, -5, or -6 (NT-3, NT-4, NT-5, or NT-6), or a nerve growth factor such as NGF-β; cardiotrophins (cardiac hypertrophy factor) such as cardiotrophin-1 (CT-1); platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; anti-HER-2 antibody; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

The preferred exogenous polypeptides of interest are mammalian polypeptides, most preferably human polypeptides. Examples of such mammalian polypeptides include t-PA, VEGF, gp120, DNase, IGF-I, IGF-II, brain IGF-I, growth hormone, relaxin chains, growth hormone releasing factor, insulin chains or pro-insulin, urokinase, immunotoxins, neurotrophins, and antigens. Particularly preferred mammalian polypeptides include, e.g., IGF-I, DNase, or VEGF, most preferably IGF-I.

As used herein, "IGF-I" refers to insulin-like growth factor from any species, including bovine, ovine, porcine, equine, and preferably human, in native-sequence or in variant form and recombinantly produced. In a preferred method, the IGF-I is cloned and its DNA expressed, e.g., by the process described in EP 128,733 published Dec. 19, 1984.

The expression "control sequences" refers to DNA sequences necessary for the expression of an operably-linked coding sequence in a particular host organism. The control sequences that are suitable for bacteria include a promoter such as the alkaline phosphatase promoter, optionally an operator sequence, and a ribosome-binding site.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading frame. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

B. Modes for Carrying Out the Invention

The present process addresses accumulation of insoluble aggregates in the bacterial periplasm and recovery of refractile particles containing an insoluble heterologous polypeptide therefrom. Chloroform is not used in any of the basic three steps of the process.

In the first step of this process, the bacterial cells, preferably non-temperature-sensitive bacterial cells, are cultured so as to express the nucleic acid encoding the polypeptide in the periplasmic space. The cells contain nucleic acid encoding a phage lysozyme, preferably T4-lysozyme, nucleic acid encoding the heterologous polypeptide, a signal sequence for secretion of the heterologous polypeptide, and separate promoters for each of the nucleic acid encoding the lysozyme and the nucleic acid encoding the heterologous polypeptide. Typically, the expression elements are introduced into the cells by transformation therein, but they may also be integrated into the genome or chromosome of the host bacterial cells along with their promoter regions. Further, the polypeptide-encoding nucleic acid and the phage-lysozyme-encoding nucleic acid may be contained on separate plasmids used to transform the cells or on one single plasmid.

In the process herein, induction of the promoters is preferred; however, the process also contemplates the use of a promoter for the lysozyme that is a promoter with low basal expression (slightly leaky), wherein no induction is carried out. This type of promoter has a leakiness that is low enough not to result in premature cell lysis and results in a sufficiently low basal expression level so as not to affect cell growth or product accumulation.

The culturing is carried out in a manner such that expression of the nucleic acid encoding the lysozyme, when induced, commences after about 50% or more of the heterologous polypeptide has accumulated, and under conditions whereby the heterologous polypeptide is secreted into the periplasm of the bacteria and the phage lysozyme accumulates in the cytoplasmic compartment.

The promoters for this process must be different, such that the nucleic-acid-encoded heterologous polypeptide expression is induced before expression of nucleic-acid-encoded phage lysozyme or at a much higher level, when the promoters are inducible. While the promoters may be any suitable promoters for this purpose, preferably, the promoters for the lysozyme and polypeptide are, respectively, arabinose promoter and alkaline phosphatase promoter. Alternatively, the compartmentalization of the phage lysozyme may allow for the use of a promoter with low basal expression for expression of the nucleic acid encoding phage lysozyme. If a promoter with low basal expression is employed, such as arabinose as opposed to tac or trp promoter, then an active step of induction is not required.

The induction of expression of the nucleic acid encoding the phage lysozyme is preferably carried out by adding an inducer to the culture medium. While, in this respect, the inducers for the promoters may be added in any amount, preferably if the inducer is arabinose, it is added in an amount of about 0-1% by weight, and if inducer is added, 0.1-1% by weight.

While the signal sequence may be any sequence, including the native signal sequence, if the polypeptide is IGF-I, preferably the signal peptide is lamB.

The culturing step takes place under conditions of high cell density, that is, generally at a cell density of about 15 to 150 g dry weight/liter, preferably at least about 40, more preferably about 40-150, most preferably about 40 to 100. In optical density, 120 OD550 ($A_{550}$) is about 50 g dry wt./liter. In addition, the culturing can be accomplished using any scale, even very large scales of 100,000 liters. Preferably, the scale is about 100 liters or greater, more preferably at least about 500 liters, and most preferably from about 500 liters to 100,000 liters.

In the process described above, the bacterial cells may be transformed with one or two expression vectors containing the nucleic acid encoding the phage lysozyme and the nucleic acid encoding the heterologous polypeptide. In one such embodiment, the bacterial cells are transformed with two vectors respectively containing the nucleic acid encoding the phage lysozyme and the nucleic acid encoding the heterologous polypeptide. Such two-plasmid system allows for the moderation of gene copy number. In another such embodiment, the nucleic acid encoding the phage lysozyme and the nucleic acid encoding the heterologous polypeptide are contained on one vector with which the bacterial cells are transformed. Alternatively, the nucleic acid encoding the phage lysozyme and/or polypeptide, along with the respective promoter(s) therefor, is integrated into the host chromosome.

In the first step, the heterologous nucleic acid (e.g., cDNA or genomic DNA) is suitably inserted into a replicable vector for expression in the bacterium under the control of a suitable promoter for bacteria. Many vectors are available for this purpose, and selection of the appropriate vector will depend mainly on the size of the nucleic acid to be inserted into the vector and the particular host cell to be transformed with the vector. Each vector contains various components depending on its function (amplification of DNA or expression of DNA) and the particular host cell with which it is compatible. The vector components for bacterial transformation will include a signal sequence for the polypeptide and will also include an inducible promoter for the polypeptide and an inducible promoter or a non-inducible one with low basal expression for the phage lysozyme. They also generally include an origin of replication and one or more marker genes.

In general, plasmid vectors containing replicon and control sequences that are derived from species compatible with the host cell are used in connection with bacterial hosts. The vector ordinarily carries a replication site, as well as marking sequences that are capable of providing phenotypic selection in transformed cells. For example, E. coli is typically transformed using pBR322, a plasmid derived from an E. coli species. See, e.g., Bolivar et al., Gene 2: 95 (1977). pBR322 contains genes conferring ampicillin and tetracycline resistance and thus provides an easy means for identifying transformed cells. The pBR322 plasmid, or other microbial plasmid or phage, also generally contains, or is modified to contain, promoters that can be used by the bacterial organism for expression of the selectable marker genes.

The DNA encoding the polypeptide of interest herein contains a signal sequence, such as one at the N-terminus of the mature polypeptide. In general, the signal sequence may be a component of the vector, or it may be a part of the polypeptide DNA that is inserted into the vector. The heterologous signal sequence selected should be one that is recognized and processed (i.e., cleaved by a signal peptidase) by the host cell. For bacterial host cells that do not recognize and process the native polypeptide signal sequence, the signal sequence is substituted by a bacterial signal sequence selected, for example, from the group consisting of the alkaline phosphatase, penicillinase, lpp, or heat-stable enterotoxin II leaders.

Expression vectors contain a nucleic acid sequence that enables the vector to replicate in one or more selected host cells. Such sequences are well known for a variety of bacteria. The origin of replication from the plasmid pBR322 is suitable for most Gram-negative bacteria.

Expression vectors also generally contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. One example of a selection scheme utilizes a drug to arrest growth of a host cell. Those cells that are successfully transformed with a heterologous gene produce a protein conferring drug resistance and thus survive the selection regimen.

The expression vector for producing a heterologous polypeptide also contains an inducible promoter that is recognized by the host bacterial organism and is operably linked to the nucleic acid encoding the polypeptide of interest. It also contains a separate promoter, which may be inducible or of low basal expression, operably linked to the nucleic acid encoding the phage lysozyme. Inducible promoters suitable for use with bacterial hosts include the β-lactamase and lactose promoter systems (Chang et al., *Nature* 275: 615 (1978); Goeddel et al., *Nature* 281: 544 (1979)), the arabinose promoter system, including the araBAD promoter (Guzman et al., *J. Bacteriol.* 174: 7716-7728 (1992); Guzman et al., *J. Bacteriol.* 177: 4121-4130 (1995); Siegele and Hu *Proc. Natl. Acad. Sci. USA*, 94: 8168-8172 (1997)), the rhamnose promoter (Haldimann et al., *J. Bacteriol.*, 180: 1277-1286 (1998)), the alkaline phosphatase promoter, a tryptophan (trp) promoter system (Goeddel, *Nucleic Acids Res.*, 8: 4057 (1980) and EP 36,776), the $P_{LtetO-1}$ and $P_{lac/ara-1}$ promoters (Lutz and Bujard, *Nucleic Acids Res.*, 25: 1203-1210 (1997)), and hybrid promoters such as the tac promoter (deBoer et al., *Proc. Natl. Acad. Sci. USA*, 80: 21-25 (1983)). However, other known bacterial inducible and low-basal-expression promoters are suitable. Their nucleotide sequences have been published, thereby enabling a skilled worker operably to ligate them to DNA encoding the polypeptide of interest or to the phage lysozyme gene (Siebenlist et al., *Cell* 20: 269 (1980)) using linkers or adaptors to supply any required restriction sites. If a strong and highly leaky promoter, such as the trp promoter, is used, it is generally used only for expression of the nucleic acid encoding the heterologous polypeptide and not for phage-lysozyme-encoding nucleic acid. The tac and $P_L$ promoters could be used for either, but not both the polypeptide and phage lysozyme, but are not preferred. Preferred are the alkaline phosphatase promoter for the product and the arabinose promoter for the phage lysozyme.

Promoters for use in bacterial systems also generally contain a Shine-Dalgarno (S.D.) sequence operably linked to the DNA encoding the polypeptide of interest. The promoter can be removed from the bacterial source DNA by restriction enzyme digestion and inserted into the vector containing the desired DNA. The phoA promoter can be removed from the bacterial-source DNA by restriction enzyme digestion and inserted into the vector containing the desired DNA.

Construction of suitable vectors containing one or more of the above-listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures are used to transform *E. coli* K12 strain 294 (ATCC 31,446) or other strains, and successful transformants are selected by ampicillin or tetracycline resistance where appropriate. Plasmids from the transformants are prepared, analyzed by restriction endonuclease digestion, and/or sequenced by the method of Sanger et al., *Proc. Natl. Acad. Sci. USA* 74: 5463-5467 (1977) or Messing et al., *Nucleic Acids Res.* 9: 309 (1981), or by the method of Maxam et al., *Methods in Enzymology* 65: 499 (1980).

Suitable bacteria for this purpose include archaebacteria and eubacteria, especially eubacteria, more preferably Gram-negative bacteria, and most preferably Enterobacteriaceae. Examples of useful bacteria include *Escherichia, Enterobacter, Azotobacter, Erwinia, Bacillus, Pseudomonas, Klebsiella, Proteus, Salmonella, Serratia, Shigella, Rhizobia, Vitreoscilla*, and *Paracoccus*. Suitable *E. coli* hosts include *E. coli* W3110 (ATCC 27,325), *E. coli* 294 (ATCC 31,446), *E. coli* B, and *E. coli* X1776 (ATCC 31,537). These examples are illustrative rather than limiting. Mutant cells of any of the above-mentioned bacteria may also be employed. It is, of course, necessary to select the appropriate bacteria taking into consideration replicability of the replicon in the cells of a bacterium. For example, *E. coli, Serratia*, or *Salmonella* species can be suitably used as the host when well-known plasmids such as pBR322, pBR325, pACYC177, or pKN410 are used to supply the replicon.

*E. coli* strain W3110 is a preferred host because it is a common host strain for recombinant DNA product fermentations. Preferably, the host cell should secrete minimal amounts of proteolytic enzymes. For example, strain W3110 may be modified to effect a genetic mutation in the genes encoding proteins, with examples of such hosts including *E. coli* W3110 strain 1A2, which has the complete genotype tonAΔ (also known as ΔfhuA); *E. coli* W3110 strain 9E4, which has the complete genotype tonAΔ ptr3; *E. coli* W3110 strain 27C7 (ATCC 55,244), which has the complete genotype tonAΔ ptr3 phoAΔE15 Δ(argF-lac) 169 ompTΔ degP41kan$^r$; *E. coli* W3110 strain 37D6, which has the complete genotype tonAΔ ptr3 phoAΔE15 Δ(argF-lac) 169 ompTΔ degP41kan$^r$ rbs7 Δ ilvG; *E. coli* W3110 strain 40B4, which is strain 37D6 with a non-kanamycin resistant degP deletion mutation; *E. coli* W3110 strain 33D3, which has the complete genotype tonA ptr3 lacIq LacL8 ompT degP kan$^r$; *E. coli* W3110 strain 36F8, which has the complete genotype tonA phoA Δ(argF-lac) ptr3 degP kan$^R$ ilvG+, and is temperature resistant at 37° C.; *E. coli* W3110 strain 45F8, which has the complete genotype fhuA(tonA) Δ(argF-lac) ptr3 degP41 (kanS) Δ omp Δ(nmpc-fepE) ilvG+ phoA+phoS*(T10Y); *E. coli* W3110 strain 43E7, which has the complete genotype fhuA(tonA) Δ(argF-lac) ptr3 degP41(kanS) ΔompTΔ(nmpc-fepE) ilvG+ phoA+; and an *E. coli* strain having the mutant periplasmic protease(s) disclosed in U.S. Pat. No. 4,946,783 issued Aug. 7, 1990.

Host cells are transformed with the above-described expression vector(s) of this invention and cultured in conventional nutrient media modified as appropriate for inducing the various promoters if induction is carried out.

Transformation means introducing DNA into an organism so that the DNA is replicable, either as an extrachromosomal element or as chromosomal integration. Depending on the host cell used, transformation is done using standard techniques appropriate to such cells. The calcium treatment employing calcium chloride, as described in section 1.82 of Sambrook et al., *Molecular Cloning: A Laboratory Manual* (New York: Cold Spring Harbor Laboratory Press, 1989), is generally used for bacterial cells that contain substantial cell-wall barriers. Another method for transformation employs polyethylene glycol/DMSO, as described in Chung and Miller, *Nucleic Acids Res.*, 16: 3580 (1988). Yet another method is the use of the technique termed electroporation.

Bacterial cells used to produce the polypeptide of interest described in this invention are cultured in suitable media in which the promoters can be induced as described generally, e.g., in Sambrook et al., supra.

Any other necessary supplements besides carbon, nitrogen, and inorganic phosphate sources may also be included at appropriate concentrations, introduced alone or as a mixture with another supplement or medium such as a complex nitrogen source. The pH of the medium may be any pH from about 5-9, depending mainly on the host organism.

For induction, typically the cells are cultured until a certain optical density is achieved, e.g., a $A_{550}$ of about 80-100, at which point induction is initiated (e.g., by addition of an inducer, by depletion of a repressor, suppressor, or medium component, etc.), to induce expression of the gene encoding the heterologous polypeptide. When about 50% or more of the polypeptide has accumulated (as determined, e.g., by the optical density reaching a target amount observed in the past to correlate with the desired polypeptide accumulation, e.g., a $A_{550}$ of about 120-140), induction of the promoter is effected for the phage lysozyme. The induction typically takes place at a point in time post-inoculation about 75-90%, preferably about 80-90%, of the total fermentation process time, as determined from prior experience and assays. For example, induction of the promoter may take place at from about 30 hours, preferably 32 hours, up to about 36 hours post-inoculation of a 40-hour fermentation process.

Gene expression may be measured in a sample directly, for example, by conventional northern blotting to quantitate the transcription of mRNA (Thomas, *Proc. Natl. Acad. Sci. USA*, 77: 5201-5205 (1980)). Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like.

For accumulation of an expressed gene product, the host cell is cultured under conditions sufficient for accumulation of the gene product. Such conditions include, e.g., temperature, nutrient, and cell-density conditions that permit protein expression and accumulation by the cell. Moreover, such conditions are those under which the cell can perform basic cellular functions of transcription, translation, and passage of proteins from one cellular compartment to another for the secreted proteins, as are known to those skilled in the art.

After accumulation of the heterologous polypeptide in the periplasm, the cells are disrupted mechanically, or lysed, to release the phage lysozyme, which in turn acts to release refractile particles containing the polypeptide from the cellular matrix, or cell wall. In a preferred embodiment, after disruption the cells are incubated for a period of time sufficient to release the heterologous polypeptide contained in the periplasm. This period of time will depend, for example, on the type of polypeptide being recovered and the temperature involved, but preferably will range from about 1 to 24 hours, more preferably 2 to 24 hours, and most preferably 2 to 3 hours. If there is overdigestion with the enzyme, the improvement in recovery of product will not be as great.

In a third step, the refractile particles released from the cellular matrix are recovered from the periplasm, in a manner that minimizes co-recovery of particulate cellular debris with the particles. The recovery may be done by any means, but preferably comprises sedimenting refractile particles containing the heterologous polypeptide or collecting supernatant containing soluble product. An example of sedimentation is centrifugation. In this case, the recovery preferably takes place in the presence of an agent that disrupts the outer cell wall to increase permeability and allows more aggregated product to be recovered. Examples of such agents include a chelating agent such as EDTA or a zwitterion such as, for example, a dipolar ionic detergent such as ZWITTERGENT 316™ detergent. See Stabel et al., supra. Most preferably, the recovery takes place in the presence of EDTA.

If centrifugation is used for recovery, the relative centrifugal force (RCF) applied is an important factor. The RCF is adjusted to minimize co-sedimentation of cellular debris with the refractile particles released from the cell wall at lysis. The specific RCF used for this purpose will vary with, for example, the type of product to be recovered, but preferably is at least about 3000×g, more preferably about 3500-6000×g, and most preferably about 4000-6000×g.

The duration of centrifugation will depend on several factors. The sedimentation rate will depend upon, e.g., the size, shape, and density of the refractile particle and the density and viscosity of the fluid. The sedimentation time for solids will depend, e.g., on the sedimentation distance and rate. It is reasonable to expect that the continuous disc-stack centrifuges would work well for the recovery of the released heterologous polypeptide aggregates or for the removal of cellular debris at large scale, since these centrifuges can process at high fluid velocities because of their relatively large centrifugal force and the relatively small sedimentation distance.

The heterologous polypeptide in aggregate form may then be further purified to obtain preparations that are substantially homogeneous as to the polypeptide of interest. In a preferred embodiment, the aggregated polypeptide is isolated, followed by a simultaneous solubilization and refolding of the polypeptide, as disclosed in U.S. Pat. No. 5,288,931.

The following procedures are exemplary of suitable purification procedures for the heterologous polypeptide once it is released from the cells: fractionation on immunoaffinity or ion-exchange columns; ethanol precipitation; reverse-phase HPLC; chromatography on silica or on a cation-exchange resin such as DEAE; chromatofocusing; SDS-PAGE; ammonium sulfate precipitation; and gel filtration using, for example, SEPHADEX™ G-75.

The following examples are offered by way of illustration and not by way of limitation. The disclosures of all patent and scientific references cited in the specification are expressly incorporated herein by reference.

EXAMPLE I

IGF-I and T4-Lysozyme Nucleic Acid Co-Expression

Background

IGF-I was selected as a first protein for evaluation of refractile particle recovery due to large-scale needs. For this evaluation, a strategy was mapped out involving genetic manipulation of the host organisms to improve the release of the refractile particles from cell-wall structures.

Materials & Methods:

pIGFLysAra Plasmid Construction: In pIGFLysAra, the IGF-I encoding sequence has a lamB signal sequence for secretion into the periplasm, and was placed behind the alkaline phosphatase promoter (AP). The T4-lysozyme gene was placed behind the ara promoter for cytoplasmic accumulation of the gene product.

Figure 1:
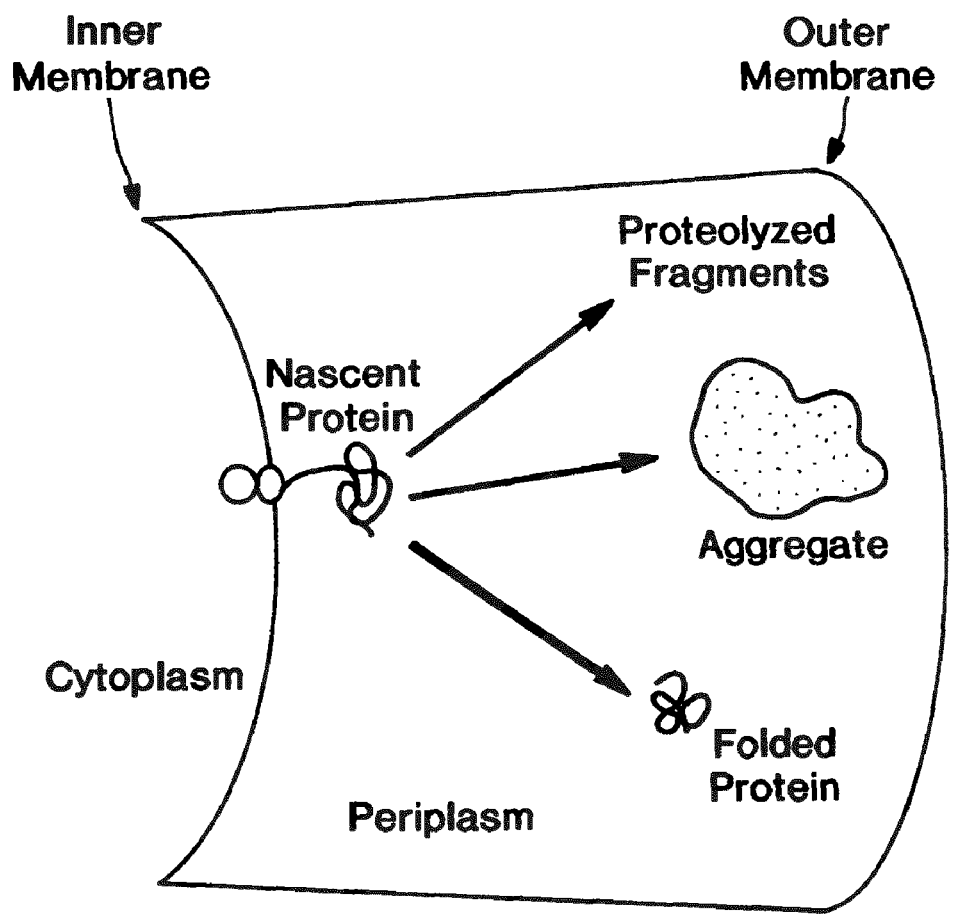
FIG. 1 depicts a schematic diagram of how a protein product is disposed in the periplasm once made in the cytoplasm, that is, it forms an aggregate, proteolyzed fragment, or folded soluble protein.
Figure 2:
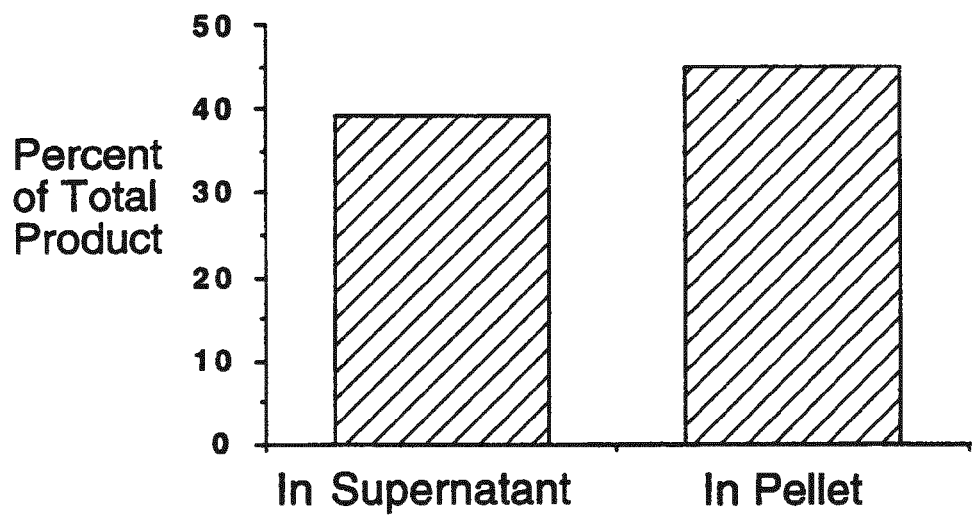
FIG. 2 depicts IGF-I aggregate recovery from the supernatant and pellet by the typical isolation procedure involving mechanical cell disruption followed by centrifugation, after three passes through the Gaulin homogenizer.
Figure 3:
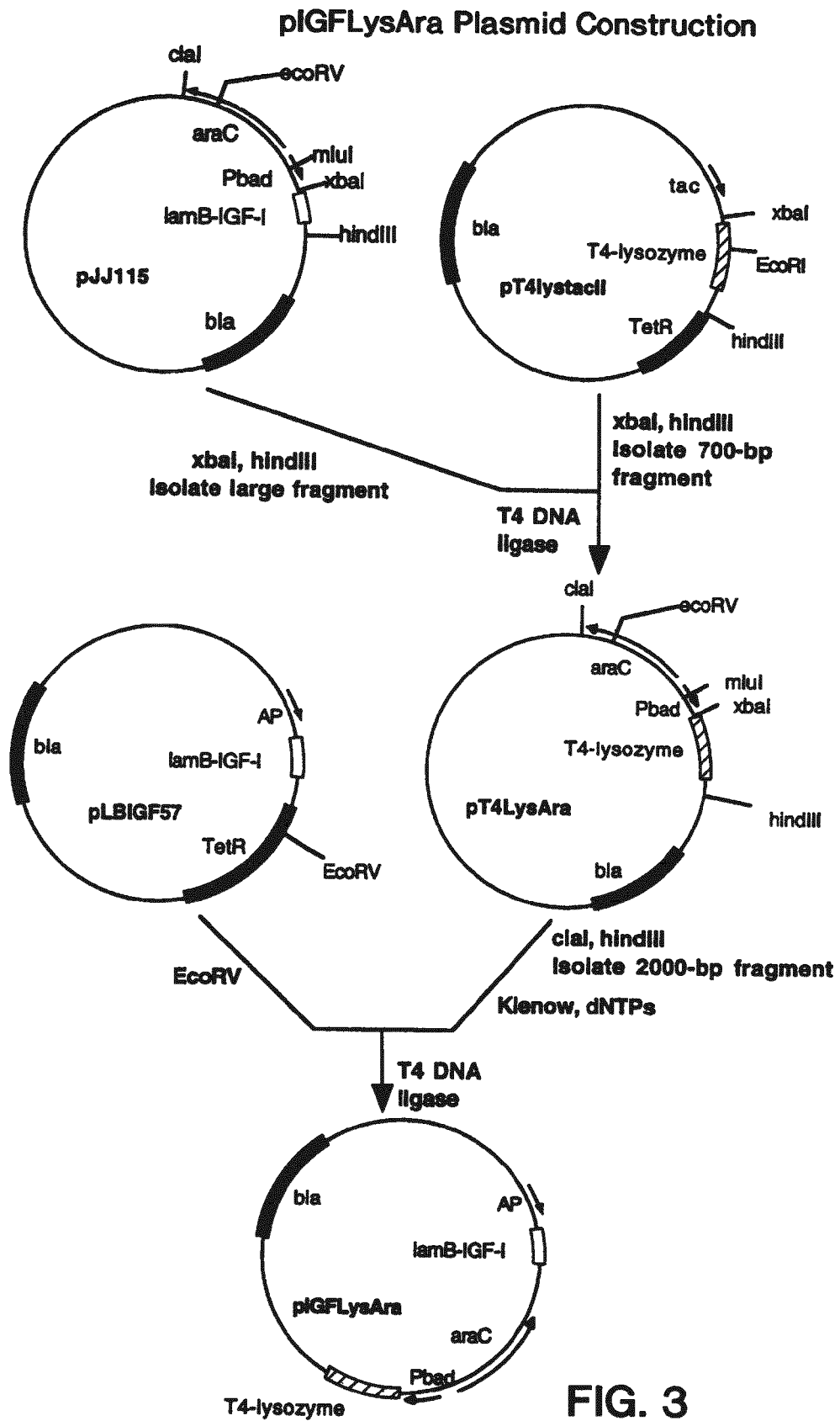
FIG. 3 depicts plasmids employed in the construction of pIGFLysAra, used to produce IGF-I, namely pJJ115, pT4lystacII, pLBIGF57, and pT4LysAra.

Details of the construction of the original plasmid, pT4lystacII, have been described in *Gene*, 38: 259-264 (1985). Intermediate plasmids were made to move the T4-lysozyme gene behind the ara promoter. Subsequently, the ara promoter-T4-lysozyme gene cassette was inserted into the IGF-I plasmid (pLBIGF57), resulting in pIGFLysAra, a single plasmid for the co-expression of nucleic acid encoding IGF-I and T4-lysozyme (FIG. 3).

The plasmid pLBIGF57 was constructed from a basic backbone of pBR322. The transcriptional and translational sequences required for the expression of nucleic acid encoding IGF-I were provided by the phoA promoter and trp Shine-Dalgarno. Secretion of the protein was directed by a TIR (translation-initiation region) variant of the lamB signal sequence. This TIR variant does not alter the primary amino acid sequence of the lamB signal; however, silent nucleotide sequence changes result, in this particular variant, in an increased level of translated protein.

The details of pLBIGF57 construction follow. A codon library of the lamB signal sequence was constructed to screen for translational initiation region (TIR) variants of differing strength. Specifically, the third position of codons 3 to 7 of the lamB signal sequence was varied. This design conserved the wild-type amino acid sequence and yet allowed for divergence within the nucleotide sequence.

LamB TIR variants were selected covering an approximate 10-fold activity range. Specifically, lamB TIR variant #57 provides an approximately 1.8 fold stronger TIR than the wild-type lamB codons based on the phoA activity assay.

The vector fragment for the construction of pLBIGF57 was generated by digesting pBK131Ran with XbaI and SphI. This XbaI-SphI vector contains the phoA promoter and trp Shine-Dalgarno sequences. The coding sequences for IGF-I and the lambda $t_o$ transcription terminator were isolated from pBKIGF-2B (U.S. Pat. No. 5,342,763) following digestion with NcoI-SphI. The lamB signal sequence fragment was isolated from pLBPhoTBK#57 (TIR variant #57; generated as described above) following digestion with XbaI-NcoI. These three fragments were then ligated together to construct pLBIGF57.

pJJ115 was constructed as follows. The ClaI/AlwNI fragment from pBR322 was inserted into ClaI/AlwNI-digested pBAD18 (Guzman et al., *J. Bacteriol.* 177: 4121-4130 (1995)) to produce pJJ70. One round of site-directed mutagenesis was then performed, changing HindIII to StuI to obtain pJJ75. A second round of site-directed mutagenesis was done to change MluI to SacII, to produce pJJ76. Then XbaI/HindIII fragments from pJJ76 and pBKIGF-2B were ligated to obtain pJJ115. A schematic of the plasmid constructions is shown in FIG. 3.

Figure 4:
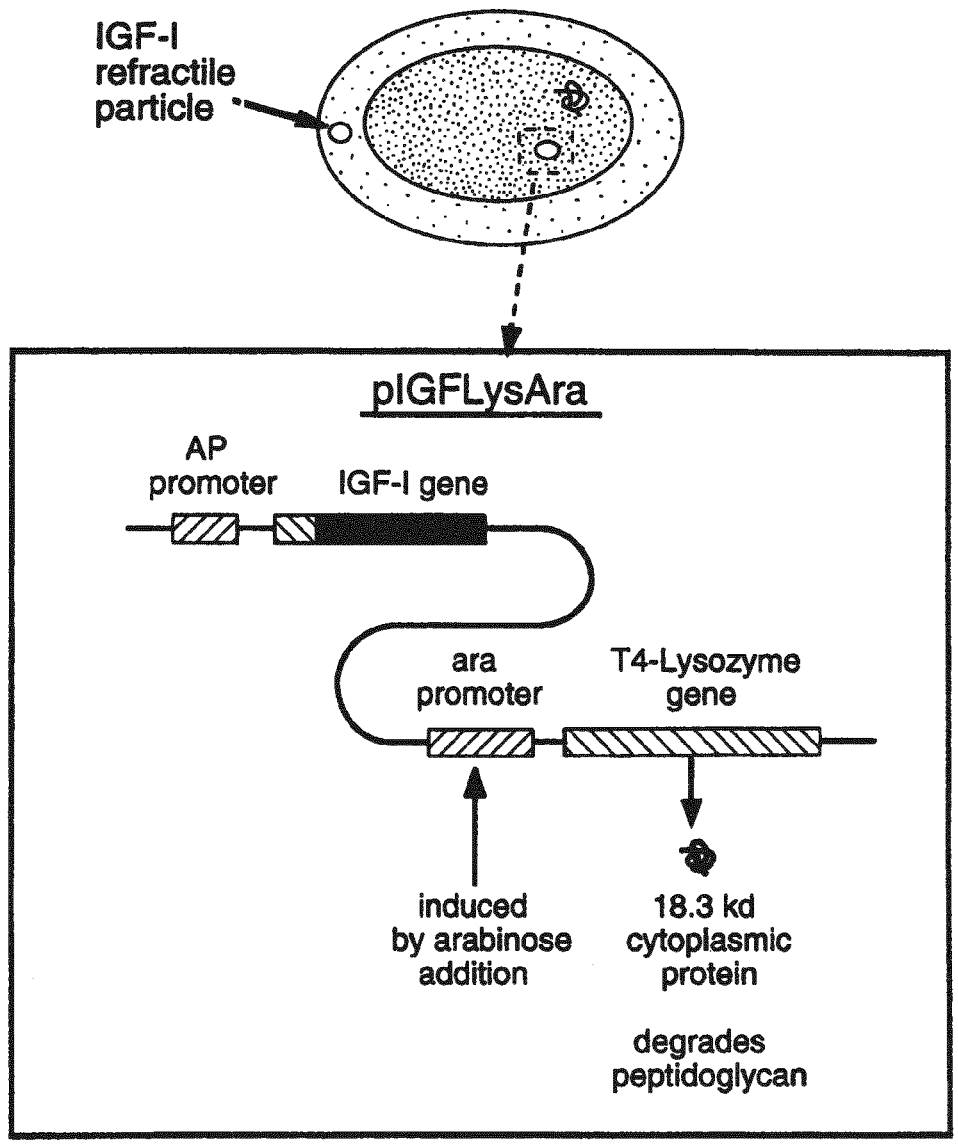
FIG. 4 depicts a schematic of the co-expression of T4-lysozyme, a preferred phage lysozyme, and IGF-I nucleic acid in accordance with an example of this invention.

FIG. 4 depicts a schematic of the co-expression of T4-lysozyme and IGF-I nucleic acid in accordance with this example.

Bacterial Strains and Growth Conditions: Most experiments were carried out with strain 45F8 (*E. coli* W3110 fhuA(tonA) Δ(argF-lac) ptr3 degP41(kanS) ΔompTΔ(nmpc-fepE) ilvG+ phoA+phoS*(T10Y)). Competent cells of 45F8 were transformed with pIGFLysAra using the standard procedure. Transformants were picked after growth on an LB plate containing 50 μg/mL carbenicillin (LB+CARB50™), streak-purified and grown in LB broth with 50 μg/mL CARB50™ in a 37° C. shaker/incubator before being tested in the fermentor.

For comparison, the IGF-I plasmid without the ara promoter-T4-lysozyme expression elements, pLBIGF57, replaced pIGFLysAra in control experiments conducted under similar conditions. pLBIGF57 confers both carbenicillin and tetracycline resistance to the production host and allows 45F8/pLBIGF57 to grow in the presence of either antibiotic.

Fermentation Process: The fermentation medium composition and experimental protocol used for the co-expression of nucleic acid encoding IGF-I and T4-lysozyme were similar to those of the scaled-down high-metabolic rate, high-yield 10-kiloliter IGF-I process. Briefly, a shake flask seed culture of 45F8/pIGFLysAra was used to inoculate the rich production medium. The composition of the medium (with the quantities of each component utilized per liter of initial medium) is described below:

| Ingredient | Quantity/L |
| --- | --- |
| Glucose* | 200-500 g |
| Ammonium Sulfate | 2-10 g |
| Sodium Phosphate, Monobasic Dihydrate | 1-5 g |
| Potassium Phosphate, Dibasic | 1-5 g |
| Sodium Citrate, Dihydrate | 0.5-5 g |
| Potassium Chloride | 0.5-5 g |
| Magnesium Sulfate, Heptahydrate | 0.5-5 g |

-continued

| Ingredient | Quantity/L |
| --- | --- |
| PLURONIC ™ Polyol, L61 | 0.1-5 mL |
| Ferric Chloride, Heptahydrate | 10-100 mg |
| Zinc Sulfate, Heptahydrate | 0.1-10 mg |
| Cobalt Chloride, Hexahydrate | 0.1-10 mg |
| Sodium Molybdate, Dihydrate | 0.1-10 mg |
| Cupric Sulfate, Pentahydrate | 0.1-10 mg |
| Boric Acid | 0.1-10 mg |
| Manganese Sulfate, Monohydrate | 0.1-10 mg |
| Hydrochloric Acid | 10-100 mg |
| Tetracycline | 4-30 mg |
| Yeast Extract* | 5-25 g |
| NZ Amine AS* | 5-25 g |
| Methionine* | 0-5 g |
| Ammonium Hydroxide | as required to control pH |
| Sulfuric Acid | as required to control pH |

*A portion of the glucose, yeast extract, NZ Amine AS, and methionine is added to the medium initially, with the remainder being fed throughout the fermentation.

The fermentation was a fed-batch process with fermentation parameters set as follow:

| | |
| --- | --- |
| Agitation: | Initially at 800 RPM, increased to 1000 RPM at 8 OD |
| Aeration: | 15.0 slpm |
| pH control: | 7.3 |
| Temp.: | 37° C. |
| Back pressure: | 0.7 bar |
| Glucose feed: | computer-controlled using an algorithm which regulates the growth rate at approximately 95% of the maximum early in the fermentation and which then controls the dissolved oxygen concentration ($DO_2$) at 30% of air saturation after the $DO_2$ drops to 30%. |
| Complex nitrogen feed: | constant feed rate of 0.5 mL/min throughout the fermentation experiment |
| Fermentation Experiment Duration: | 40 hours |

Figure 5:
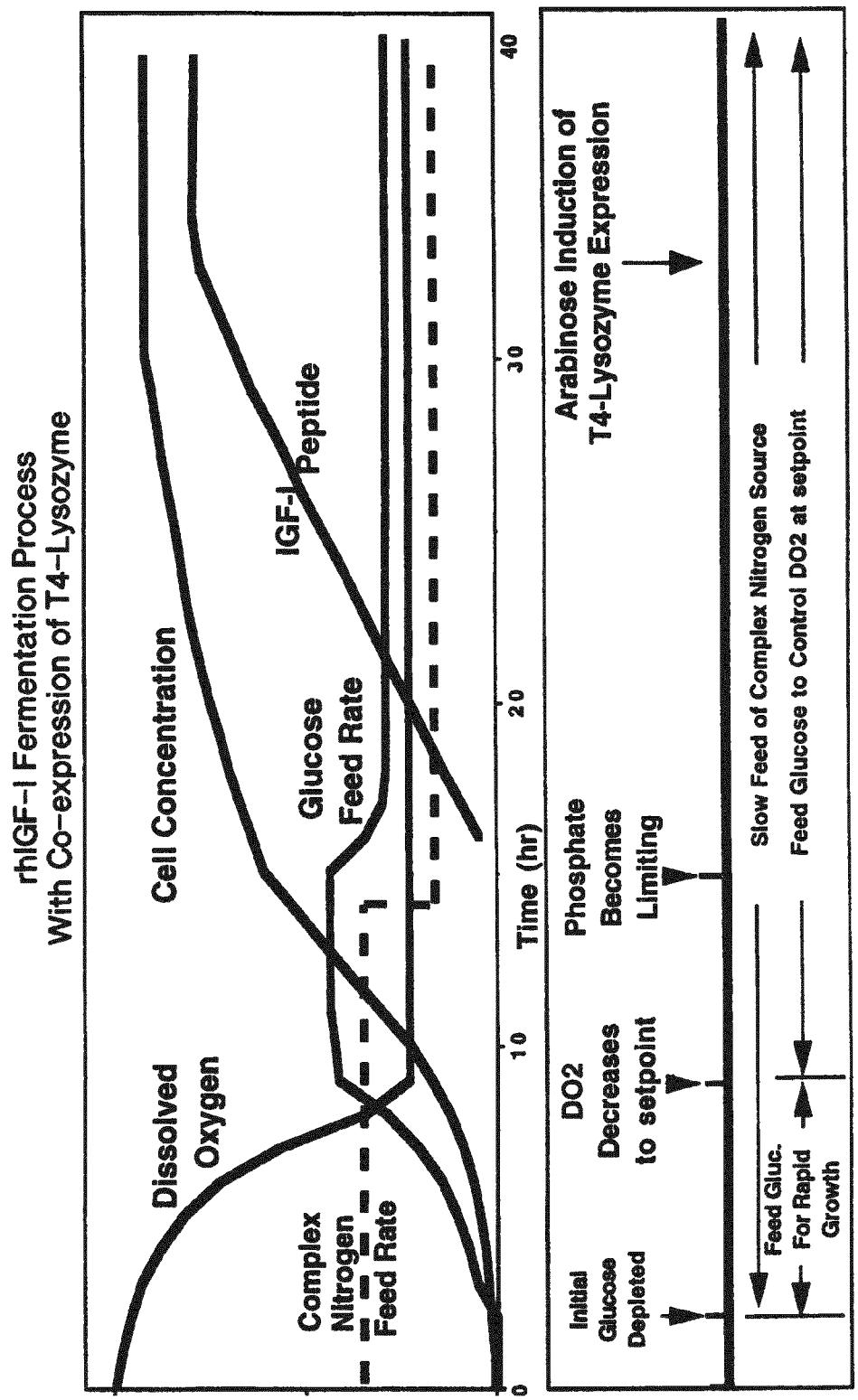
FIG. 5 depicts a graph of various parameters of the fermentation process for IGF-I using co-expression of T4-lysozyme nucleic acid with IGF-I nucleic acid for a fermentation experiment disclosed herein.

The timing of arabinose addition ranged from 24 hr to 36 hr. Bolus additions of 0.1% to 1% (final concentration) arabinose were tested to help define the induction strength necessary for producing the most preferred amounts of T4-lysozyme for better product recovery at the centrifugation step. A schematic of the fermentation process is shown in FIG. 5.

Recovery of Refractile Particle from Harvested Broth: Broth harvested at the end of fermentation was either processed soon after or stored briefly at 4° C. prior to use. The test protocol used involved four process steps:

I. Break cells open by multiple passes through the MICROFLUIDIZER® mechanical disruption device (Microfluidics, Inc., Newton, Mass.) to release T4-lysozyme from the cytoplasmic compartment of cells. This operation was carried out at room temperature instead of 4° C. to accelerate the enzymatic degradation of peptidoglycan by T4-lysozyme.

II. Add 1M EDTA to the broth passed through the MICROFLUIDIZER® device (microfluidized broth) to bring the final concentration of EDTA to 5 mM. EDTA chelates the divalent cations and disrupts the outer cell surface structure. This makes the peptidoglycan layer inside unbroken cells accessible to degradation by T4-lysozyme and weakens the cell wall to promote cell lysis.

III. Hold the lysate at room temperature or incubate at 37° C. for further degradation of cell wall. This step was introduced to simulate the longer process times associated with the larger-scale process and to evaluate product stability in the lysate.

IV. Recover refractile particles from the lysate by centrifugation. Bench-scale centrifugation in a SORVALL™ GSA rotor at two speeds (5000 rpm & 4000 rpm; equivalent to RCF's of 4056×g and 2603×g at rmax, respectively) was used to collect the solids as pellets.

An additional step to wash the pellet with buffer was investigated to purify the refractile particles further. This step would remove the lysate entrained by the pellet and minimize the amount of contaminating E. coli proteins in the refractile particle preparations.

Aliquots of the treated broth were saved after three passes through the MICROFLUIDIZER® device and after each subsequent treatment step. Samples were evaluated for the percent of the whole broth recovered in the pellet by centrifugation (% pellet). Dry weights of samples were determined by measuring the net sample weights before and after drying for a minimum of two days in a vacuum oven controlled at approximately 60-70° C. Ratio of the dried weight to that of the wet weight for the sample was expressed as percentage and reported as the % dry weight for the sample analyzed. The amount of product present in the samples was analyzed by a HPLC reverse-phase method. Product recovery efficiency was calculated by expressing the amount of product recovered by the process step as a percent of the total product present in the starting material, the fermentation broth at harvest. To evaluate the quality of the refractile particle recovered, the protein profile of refractile particles resuspended in 50 mM Tris, pH 7.5 w/5 mM EDTA to the original volume was compared to that of the harvest broth sample by gel electrophoresis in 10-20% TRICINE™ pre-cast gels (Novex). By densitometry, the percentage of the total protein represented by the product could be calculated.

Results & Discussion:
Fermentation and IGF-I Production:

The initial growth rate of 45F8/pIGFLysAra showed no significant difference from that of the 45F8/pLBIGF57 control in the fermentation process described. As expected, broth cell density reached over 120 OD550 after 14 to 16 hrs. Cell density subsequently peaked and remained steady to the end of the experiment (FIG. 6).

Typical respiration rates were obtained for both fermentations. There was a slight, but continuous drop in oxygen uptake rate (OUR, mmoles/L-min) after 32 to 34 hrs post inoculation in most experiments (FIG. 7). As this loss in respiration was seen with both experimental and control experiments, the phenomenon was probably not caused by T4-lysozyme nucleic acid co-expression.

To avoid competition for the host's synthetic capacity, T4-lysozyme nucleic acid expression, regulated by the controllable pBAD (arabinose) promoter, was to be induced by the addition of the arabinose after product accumulation stopped. However, there were indications of leaky expression of nucleic acid encoding T4-lysozyme. A slight leakage of T4-lysozyme from the cytoplasmic compartment was also suggested. The most direct evidence came from light microscopy images of cells carrying the T4-lysozyme nucleic acid expression elements. Broth samples taken prior to induction showed a small number of round-shaped cells mixed with the typical rod-shaped cells expected for E. coli. No round-shaped cells were visible in the control broth. Without being limited to any one theory, most likely, in these round cells, T4-lysozyme-encoding nucleic acid was expressed prematurely and leaked into the periplasm, compromising the peptidoglycan layer to weaken the mechanical support required for maintenance of the rod shape.

The notion of T4-lysozyme leakage was further supported by the observation of increased broth viscosity in harvested broth of 45F8/pIGFLysAra upon extended storage at 4° C. The same was not seen with fermentation broth of 45F8/pLBIGF57. Some cell walls weakened by T4-lysozyme leakage apparently were no longer able to contain the cytoplasmic turgor pressure. Release of DNA and other cytoplasmic contents by the lysed cells resulted in an increase in fluid viscosity. Also, based on the profile of oxygen transfer during fermentation by plotting kla (a measurement of oxygen transfer capacity) against experiment time, there appeared to be a decline in kla that correlated with the arabinose induction in experiments co-expressing nucleic acid encoding T4-lysozyme (FIG. 8). The loss in oxygen transfer could be explained by an increase in broth viscosity caused by T4-lysozyme-induced cell lysis.

Except for one case, the co-expression of T4-lysozyme nucleic acid had no impact on IGF-I accumulation (FIG. 9). When 0.1% arabinose was added to the culture 24 hrs after inoculation, the accumulation of IGF-I ceased soon after the arabinose addition. Under control conditions, IGF-I synthesis begins when the medium is depleted of free phosphates (typically around 12-14 hrs). By about 30-32 hrs post inoculation, the cells have accumulated the majority of the IGF-I found in the harvested broth. By this time, IGF-1-specific productivity drops off significantly. Without being limited to any one theory, one possible explanation for the yield loss associated with the 0.1% arabinose induction at 24 hrs might be that T4-lysozyme synthesis competed against IGF-I synthesis for the protein synthesis machinery remaining in the cells. When the arabinose addition was made after 32 hrs, the impact of T4-lysozyme nucleic acid expression became insignificant since only minimal amounts of IGF-I were being made at this time.

FIG. 10 shows a schematic of the process shown by this Example, with downstream processing indicated as an inventory step or protein folding after the centrifugation (recovery) step.

FIGS. 11A and 11B show respectively the percent of total product recovered and of insoluble product recovered after 0 to 2 hours of incubation at 37° C. for 0.1% ara at 32 hours and 1% ara at 36 hours. It is clear that percent product recovered increases with incubation, and 1% ara at 36 hours increased recovery at all incubation conditions except for percent of insoluble product recovered after two hours, where the 0.1% ara showed increased product recovery.

T4-lysozyme-encoding nucleic acid expression was qualitatively demonstrated by 10-20% TRICINE™ gel electrophoresis. Samples taken from experiments with earlier or stronger arabinose inductions (SI1547 induced at 24 hrs w/0.1% arabinose; SI1610 induced at 32 hr w/1%) showed in their protein profile a new protein band with the expected molecular weight of 18.3 kilodaltons for T4-lysozyme. Cells at these stages during fermentation were relatively healthy and capable of limited synthesis of T4-lysozyme upon induction. When induction was delayed to 36 hrs, no T4-lysozyme band was visible by gel analysis.

Under the fermentation and induction conditions used, T4-lysozyme was not expected to accumulate in substantial quantities. With the high specific activity of T4-lysozyme against the E. coli peptidoglycan, a small amount of T4-lysozyme is expected to be sufficient for the desired degradation of the cell wall.

Recovery of Refractile Particle from Harvested Broth:

For insoluble material, the refractile particle recovery process takes advantage of the stable nature of proteins sequestered as insoluble aggregates. The bench-scale cell disruption process was performed at room temperature in the absence of temperature control. Cell lysate exiting from the mechanical device was slightly warm to the touch. Under these conditions, the breakdown of the peptidoglycan matrix by the T4-lysozyme began immediately upon release of T4-lysozyme and was not retarded by the cooling typically employed to minimize protein denaturation and degradation by proteases.

As broth was sent through the MICROFLUIDIZER® device, there appeared to be an increase in viscosity immediately after the first passage. There were small amounts of gelatinous mass within the lysed broth that disappeared with time or after additional passes. After the second pass, the viscosity of the lysed broth appeared to have decreased. Photos taken of IGF-I cells induced for T4-lysozyme revealed good cell breakage efficiency. However, the released refractile particles appeared to have clumped together in some samples.

With the typical working volume at the start of the refractile particle recovery process of two liters, the bench-scale step of passing the broth through the MICROFLUIDIZER® device usually required less than an hour for completing three passes of the treated broth. For simulation of larger-scale processing that would take longer, a hold (incubation) step, also serving as additional reaction time for the lysozymal degradation of peptidoglycan, was introduced prior to the centrifugation step. In this study, hold times of 0, 2-3 and 24 hours were tested. Solids and product recoveries by centrifugation at two different speeds from these treated broths are summarized in Tables 1 and 2.

After centrifugation at approximately 4000×g (GSA rotor at 5000 rpm) for 30 min (Table 1), the control broth with no T4-lysozyme nucleic acid expression elements on the plasmid (45F8/pLBIGF57 as production organism) yielded a much smaller pellet by wet weight than any of the broths with some level of T4-lysozyme nucleic acid co-expression. Similar results were obtained for the percent dry weight represented by the pellet. The percentage of cell-associated IGF-I product recovered in the pellet differed significantly between these experimental conditions. When centrifugation was performed immediately after passage through the MICROFLUIDIZER® device, only 26-28% of the cell-associated IGF-I in the starting material was recovered in the pellet for the control (45F8/pLBIGF57). As much as three times that amount was recovered from the 45F8/pIGFLysAra culture grown without arabinose induction; it is likely there was leaky expression of nucleic acid encoding T4-lysozyme. With a 2-3-hour incubation prior to centrifugation, greater than 90% of total cell-associated IGF-I was found in the pellet. Further extension of the incubation time from 2-3 hours to 24 hours had little effect.

Solids recovery from treated broths by centrifugation was also tested at lower speed, approximately 2600×g for 30 min (Table 2). The resulting pellets collected were significantly smaller. The lower g-force was generally insufficient to sediment the solids suspended in the lysed broth, and therefore product recovery was poor.

The recovery of solids by centrifugation is governed by the physical properties of both the solids and the fluid in the suspension. The settling velocity of the particles is defined by the following equation:

Settling Velocity of the Particle ($v_c$)

$$v_c = \frac{(\rho_p - \rho_m)d^2\omega^2 r}{18\mu}$$

where $\rho_p$=particle density, $\rho_m$=fluid density, $\mu$=fluid viscosity, $\omega$=angular velocity, d=particle diameter, and r=radial distance.

According to this equation, while the diameter of the particle is the most important factor governing the settling velocity of the particle, the settling velocity of the particle is directly proportional to the difference between the densities of the particle and the fluid and is inversely proportional to the viscosity of the fluid containing the particle.

The refractile particles of IGF-I have been shown by electron microscopy to be large, dense globules. Other work had suggested that the density of IGF-I refractile particles was higher than that of the *E. coli* cell wall. These properties of the IGF-I refractile particles should make them amenable to efficient recovery by centrifugation. However, if the refractile particles have not been cleanly released from the cell wall at the cell lysis step, the refractile particles trapped by intact cells and cell wall debris will behave as composites and co-sediment with other solids. After digestion of the peptidoglycan layer with T4-lysozyme, if successfully freed from cellular matrix, the settling velocity of the freed IGF-I refractile particles, now being solely determined by its intrinsic physical properties, is higher than that of *E. coli* cell wall fragments. Centrifugation parameters may be manipulated to minimize co-sedimentation of cell debris with the freed refractile particles. The success of this genetic solution involving T4-lysozyme nucleic acid co-expression is evident from the greater than 95% product recovery shown in Table 1.

TABLE 1

Recovery of Solids from Microfluidized Broth (Three Passes) by Bench-Scale Centrifugation
SORVALL ™ GSA rotor, 5000 RPM for 30 min (4056 × g at $r_{max}$) at 4-15° C.

| Experiment No. | Production Organism | Induction Conditions | Hold Time(hr)[a] | % Pellet Recovered[b] | % Dry Weight[c] | % Cell-Associated IGF-I Recovery |
|---|---|---|---|---|---|---|
| (Typical Non-microfluidized Control Whole Broth) | | | | 18-23 | 8.0-8.9 | 100 |
| SI1613 | 45F8/pLBIGF57 | Control organism, no ara | 0 | 4.7 | ND | 26.0 |
| SI1624 | 45F8/pLBIGF57 | Control organism, no ara | 0 | 4.8 | 1.31 | 28.2 |
| SI1609 | 45F8/pIGFLysAra | Minus ara control | 0 | 8.7 | 2.23 | 76.3 |
| SI1610 | 45F8/pIGFLysAra | 1% ara @ 32 hrs | 0 | 5.3 | 1.58 | 47.6 |
| SI1624 | 45F8/pLBIGF57 | Control organism, no ara | 2-3 | 6.8 | 1.57 | 33.4 |
| SI1609 | 45F8/pIGFLysAra | Minus ara control | 2-3 | 11.8 | 2.49 | 95.8 |
| SI1599 | 45F8/pIGFLysAra | 0.1% ara @ 32 hrs | 2-3 | 11.4 | 2.72 | 98.3 |
| SI1610 | 45F8/pIGFLysAra | 1% ara @ 32 hrs | 2-3 | 7.9 | 1.95 | 59.7 |
| SI1602 | 45F8/pIGFLysAra | 1% ara @ 36 hrs | 2-3 | 10.2 | 2.26 | 90.2 |
| SI1613 | 45F8/pLBIGF57 | Control organism, no ara | 24 | 7.8 | 1.93 | 35.8 |

TABLE 1-continued

Recovery of Solids from Microfluidized Broth (Three Passes) by Bench-Scale Centrifugation
SORVALL ™ GSA rotor, 5000 RPM for 30 min (4056 × g at $r_{max}$) at 4-15° C.

| Experiment No. | Production Organism | Induction Conditions | Hold Time(hr)[a] | % Pellet Recovered[b] | % Dry Weight[c] | % Cell-Associated IGF-I Recovery |
|---|---|---|---|---|---|---|
| SI1609 | 45F8/pIGFLysAra | Minus ara control | 24 | 12.3 | 2.75 | 90.8 |
| SI1610 | 45F8/pIGFLysAra | 1% ara @ 32 hrs | 24 | 10.8 | 2.51 | 81.1 |

Footnotes to Table 1:
[a]Microfluidized broth was held at 37° C. for the first three hours and transferred to room temperature for the remaining time prior to centrifugation to help determine the best exposure of lysed broth to released T4-lysozyme required for efficient refractile particle recovery at the centrifugation step.
[b]Percent pellet recovered is the percent of the whole broth recovered in the pellet by centrifugation.
[c]Percent dry weight is the ratio × 100 of the dried weight to the initial wet weight for the sample (fermentation broth), where the dry weight is determined as described above.

TABLE 2

Recovery of Solids from Microfluidized Broth (Three Passes) by Bench-Scale Centrifugation
SORVALL ™ GSA 4000 RPM for 30 min (2603 × g at $r_{max}$) at 4-15° C.

| Experiment No. | Production Organism | Induction Conditions | Hold Time(hr)[a] | % Pellet Recovered[b] | % Dry Weight[c] | % Cell-Associated IGF-I Recovery |
|---|---|---|---|---|---|---|
| | (Typical Non-microfluidized Control Whole Broth) | | | 18-20 | 8.0-8.9 | 100 |
| SI1613 | 45F8/pLBIGF57 | Control organism, no ara | 0 | 2.4 | ND | 17.7 |
| SI1553 | 45F8/pLBIGF57 | Minus ara control | 1 | 3.2 | 1.14 | >36.0 |
| SI1599 | 45F8/pIGFLysAra | 0.1% ara @ 32 hrs | 1 | 6.0 | 1.41 | 19.5 |
| SI1554 | 45F8/pIGFLysAra | 1% ara @ 32 hrs | 1 | 3.8 | 1.18 | 26.3 |
| SI1547 | 45F8/pLBIGF57 | 0.1% ara @ 24 hrs | 1 | 2.1 | 0.90 | 15.5 |
| SI1613 | 45F8/pIGFLysAra | Control organism, no ara | 24 | 5.7 | 1.51 | 24.9 |
| SI1609 | 45F8/pIGFLysAra | Minus ara control | 24 | 13.1 | ND | ND |
| SI1610 | 45F8/pIGFLysAra | 1% ara @ 32 hrs | 24 | 11.6 | ND | ND |

[a]Microfluidized broth was held at 37° C. for the first three hours and transferred to room temperature for the remaining time prior to centrifugation to help determine the best exposure of lysed broth to released T4-lysozyme required for efficient refractile particle recovery at the centrifugation step.
[b]Percent pellet recovered is the percent of the whole broth recovered in the pellet by centrifugation.
[c]Percent dry weight is the ratio × 100 of the dried weight to the initial wet weight for the sample (fermentation broth), where the dry weight is determined as described above.

T-4 Lysozyme vs. HEW-Lysozyme:

The effectiveness of endogenous T4-lysozyme versus the exogenous HEW-lysozyme on the recovery of IGF-I refractile particles was compared in Table 3, and shown in a bar graph in FIG. 12. As a replacement for T4-lysozyme, HEW-lysozyme was added to 0.2 mg/mL (final concentration) (previously found to be the optimal concentration for cell lysis) to microfluidized control broth (45F8/pLBIGF57 that had its pH adjusted to 9.0). The resultant broth was carried through the remaining recovery steps alongside the T4-lysozyme-containing broths. As shown in Table 3, addition of HEW-lysozyme increased the % of cell-associated IGF-I recovered from 28-33% for the control case to 42-52%. However, compared to the greater-than-90% product recovery for broths with T4-lysozyme nucleic acid co-expression, HEW-lysozyme treatment was clearly and unexpectedly much inferior.

The protein profile of the recovered IGF-I refractile particle was examined by 10-20% TRICINE™ gel electrophoresis. The pellets collected by centrifugation were resuspended in buffer to the original volume, allowing for direct comparison to the control samples. Gel analysis of the various β-mercaptoethanol-reduced refractile particle samples showed a significant clean-up compared to the whole broth control. In general, there was little qualitative difference between samples held for a wide range of times for extended enzymatic degradation of peptidoglycan by the T4-lysozyme. The T4-lysozyme was highly efficient in releasing the refractile particles from cells.

TABLE 3

Effectiveness of Endogenous T4-lysozyme vs Exogenous HEW-Lysozyme on IGF-I Refractile Particle
Recovery from Microfluidized Broth[a] (Three Passes) by Bench Scale Centrifugation
SORVALL ™ GSA rotor, 5000 RPM for 30 min (4056 × g at $r_{max}$) at 4-15° C.

| Experiment No. | Production Organism | Induction Conditions | Hold Time (hr)[b] | % Pellet Recovered[c] | % Dry Weight[d] | % Cell-Associated IGF-I Recovery |
|---|---|---|---|---|---|---|
| | (Typical Non-microfluidized Control Whole Broth) | | | 18-23 | 8.0-8.9 | 100 |
| SI1624 | 45F8/pLBIGF57 | Control organism, no araNo lysozyme, no EDTA | 0 | 4.8 | 1.31 | 28.2 |
| | | | 2 | 6.8 | 1.57 | 33.4 |
| | | 0.2 mg/mL HEW-lysozyme plus EDTA | 0 | 6.2 | 1.62 | 42.9 |
| | | | 2 | 7.0 | 1.70 | 51.9 |
| SI1599 | 45F8/pIGFLysAra | 0.1% ara @ 32 hrsT4-lysozyme plus EDTA | 0 | 4.6 | 1.26 | 38.0 |
| | | | 2 | 11.4 | 2.72 | 98.3 |

TABLE 3-continued

Effectiveness of Endogenous T4-lysozyme vs Exogenous HEW-Lysozyme on IGF-I Refractile Particle
Recovery from Microfluidized Broth[a] (Three Passes) by Bench Scale Centrifugation
SORVALL ™ GSA rotor, 5000 RPM for 30 min (4056 × g at $r_{max}$) at 4-15° C.

| Experiment No. | Production Organism | Induction Conditions | Hold Time (hr)[b] | % Pellet Recovered[c] | % Dry Weight[d] | % Cell-Associated IGF-I Recovery |
|---|---|---|---|---|---|---|
| SI1602 | 45F8/pIGFLysAra | 1% ara @ 36 hrsT4-lysozyme plus EDTA | 0 | 8.4 | 1.95 | 88.3 |
|  |  |  | 2 | 10.2 | 2.26 | 90.2 |

[a]The typical starting working volume was 2 L of harvest broth and the step of passing through the MICROFLUIDIZER ® device usually required 30 to 45 min.
[b]Microfluidized broth was held at 37° C. for degradation of peptidoglycan by released T4-lysozyme or added HEW-lysozyme prior to recovering refractile particles at the centrifugation step.
[c] and [d]See footnotes b and c of Table 1.

EXAMPLE II

VEGF or DNase and T4-Lysozyme Nucleic Acid Co-Expression

Background

It was important to determine if the T4-lysozyme nucleic acid co-expression technology had general application across other processes involving refractile particles. E.-coli-produced VEGF (a 21 kD protein) and DNase (a 31.9-kilodalton protein) were two additional products known to accumulate in the periplasmic space as refractile particles and therefore suitable proteins for evaluation. It was difficult to predict if T4-lysozyme nucleic acid co-expression would bring similar benefits to product recovery since it was not known if the physical properties of the refractile particles of VEGF and DNase differ significantly from that of the IGF-I refractile particles.

For efficient evaluation of the T4-lysozyme nucleic acid co-expression approach in multiple processes, a separate plasmid for the expression of nucleic acid encoding T4-lysozyme, pJJ153, was constructed. It was used in the co-transformation of the appropriate host organism along with the product plasmid encoding either VEGF (pVEGF171) or DNase (pLS20).

Materials and Methods:

pJJ153 Plasmid Construction: The construction of pJJ153 (a pACYC177 derivative that is compatible with pBR322 vectors) is shown in FIG. 13. The ClaI/AlwNI fragment from pBR322 was inserted into ClaI/AlwNI-digested pBAD18 (Guzman et al., supra) to produce pJJ70. One round of site-directed mutagenesis was then performed, changing HindIII to StuI to obtain pJJ75. A second round of site-directed mutagenesis was done to change MluI to SacII, to produce pJJ76. Then XbaI/HindIII fragments from pJJ76 and from pBKIGF2B were ligated, and XbaI/HindIII fragments from this ligation product and from a T4-lysozyme/tac plasmid were ligated to produce pT4LysAra. Then BamHI (filled in)/ScaI-digested pACYC177 was ligated with ClaI/HindIII (both ends filled in)-digested pT4LysAra to produce pJJ153. The maps for pACYC177, pT4LysAra, and pJJ153 are shown in FIG. 13.

pVEGF171 Plasmid Construction: The construction of pVEGF171 is as follows: pVEGF171 is a derivative of the previously published VEGF165 plasmid with a TIR relative strength of 3 (Simmons et al., *Nature Biotechnology* 14:629-634 (1996)). In this plasmid the mature VEGF coding sequence (Leung et al., *Science* 246:1306-1309 (1989)) is preceded by that of the STII signal sequence (Picken et al., *Infect. Immun.* 42:269-275 (1983); Lee et al., *Infect. Immun.* 42:264-268 (1983)) to provide for secretion of VEGF into the E. coli periplasmic space. Transcription of the heterologous gene is provided for by the alkaline phosphatase promoter (Kikuchi et al., *Nucleic Acids Res.,* 9:5671-5678 (1981)), and translation initiation is controlled by the silent codon changes in the STII signal sequence as noted (Simmons et al., *Nature Biotechnology,* 14:629-634 (1996)). The only change in pVEGF171 from the above-described VEGF165 plasmid is the addition of the λ to transcriptional terminator (Scholtissek et al., *Nucleic Acids Res.* 15:3185 (1987)) just downstream of the VEGF termination codon, followed by the fully restored tetracycline resistance gene of pBR322 (Bolivar et al., *Gene* 2:95-113 (1977)).

pLS20 Plasmid Construction: The plasmid pLS20 is a pBR322 (Sutcliffe, *Cold Spring harbor Symp. Quant. Biol.,* 43: 77-90 (1978)))-based plasmid designed for the expression of DNase in *E. coli*. The transcriptional and translational sequences required for the expression of DNase are provided by the alkaline phosphatase promoter, the trp Shine-Dalgarno and the STII Shine-Dalgarno, as described for the plasmid phGH1 (Chang et al., *Gene,* 55: 189-196 (1987)). Secretion of the protein from the cytoplasm to the periplasmic space is directed by the STII signal sequence (Picken et al., *Infect. Immun.,* 42: 269-275 (1983)). Downstream of the DNase coding sequence is the tetracycline resistance gene. The forward and complementary nucleotide sequences (SEQ ID NOS:1 and 2, respectively) and the amino acid sequence (SEQ ID NO:3) for the STII signal sequence and DNase are provided in FIG. 14.

The construction of pLS20 is as follows: The vector fragment for the construction of pLS20 was generated by digesting pTF111 with NsiI-BamHI and isolating the largest fragment. The plasmid pTF111 is a derivative of phGH1 (Chang et al., supra), and an identical vector would have been generated had phGH1 been used in place of pTF111. The second fragment required for this construction was isolated from pLS18 following digestion with NsiI-HindIII. The HindIII site of this fragment was blunted by treatment with DNA Polymerase I (Klenow). The coding sequence for DNase is contained within this approximately 790-bp fragment. The final fragment necessary for the ligation was generated by digesting pBR322 with EcoRI-BamHI. The EcoRI site of this fragment was blunted by treatment with DNA Polymerase I (Klenow). This fragment of approximately 380 bp contained the tetracycline-resistance promoter and the 5' end of the tetracycline-resistance coding sequence. These three fragments were ligated together as illustrated in FIG. 15 to construct pLS20.

Bacterial strains and growth conditions: Both the VEGF and DNase fermentations conducted for this example used strain 43E7 as production host (*E. coli* W3110 fhuAtonA Δ(argF-lac) 169 ptr3 degP41(kanS) ΔompTL(nmpc-fepE) ilvG+ phoAΔE15). Competent cells of 43E7 were transformed with pJJ153 and either pVEGF171 or pLS20 using standard procedures. Transformants were picked from LB plates containing 20 μg/mL tetracycline and 50 μg/mL kanamycin (LB+Tet20+Kan50), streak-purified, and grown in LB broth with 20 μg/mL tetracycline and 50 μg/mL kanamycin in a 37° C. or 30° C. shaker/incubator before being stored in DMSO at −80° C.

For control conditions, the host 43E7 transformed with either pVEGF171 or pLS20 alone was used for the VEGF or DNase processes, respectively.

VEGF Fermentation Process: The fermentation medium composition and experimental protocol used for the co-expression of VEGF and T4-lysozyme nucleic acids were as follows. A shake flask seed culture of 43E7/pVEGF171 or 43E7/pVEGF171/pJJ153 was used to inoculate the rich selective production medium, and the fermentation parameters were set as follows:

| | |
|---|---|
| Agitation: | 1000 RPM |
| Aeration: | 10.0 slpm |
| pH control: | 7.2 |
| Temp.: | 37° C. |
| Back pressure: | 0.3 bar |
| Glucose feed: | computer controlled, initially using an algorithm to control the culture near its maximum growth rate without glucose overfeeding. When the $DO_2$ reaches 30% of air saturation, the algorithm adjusts the glucose feed rate to maintain the $DO_2$ at 30%. |
| Fermentation experiment duration: | 40 hours |

1% arabinose additions were made at 26 hr or 32 hr post inoculation for the induction of T4-lysozyme nucleic acid expression.

DNase Fermentation Process: A shake flask seed culture of 43E7/pLS20 or 43E7/pLS20/pJJ153 grown in LB plus the appropriate antibiotics was used to inoculate the rich selective production medium in the fermentor, and the fermentation parameters were set as follow:

| | |
|---|---|
| Agitation: | 1000 RPM |
| Aeration: | 10.0 slpm |
| pH control: | 7.2 |
| Temp.: | 30° C. |
| Back pressure: | 0.3 bar |
| Glucose feed: | computer controlled, initially using an algorithm to control the culture near its maximum growth rate without glucose overfeeding. When the $DO_2$ reaches 30% of air saturation, the algorithm adjusts the glucose feed rate to maintain the $DO_2$ at 30%. |
| Complex nitrogen feed: | 0.25 mL/min starting at 20 OD |

1% arabinose addition was made at 24 hr or 32 hr post inoculation for the induction of T4-lysozyme nucleic acid expression. Broth was harvested at 32 to 36 hrs post inoculation for refractile particle recovery evaluation.

Recovery of Refractile Particles from Harvested VEGF and DNase Broth: Broth harvested at the end of the fermentations was either processed fresh or stored briefly at 4° C. prior to use. The test protocol described earlier for IGF-I refractile particle recovery evaluation was used for the evaluation of refractile particle recovery from the VEGF and DNase broths.

Results:

Fermentation Process:

Growth of the VEGF and the DNase cultures induced for T4-lysozyme nucleic acid co-expression (directed by pJJ153) looked similar to the respective minus-pJJ153 controls. All of the VEGF and DNase fermentations showed an aggressive drop in OUR (mmoles/L-min) late in the fermentation process. At the same time, optical density ($OD_{550}$) also declined significantly. Such dramatic loss in cell density was not observed for IGF-I, a fed-batch process with a single plasmid for the co-expression of nucleic acid encoding the product and T4-lysozyme.

In experiment SRPVF2, 1% arabinose was added at 32 hr post inoculation for the induction of T4-lysozyme nucleic acid co-expression, well after the respiration rate of the cells had started to decline. T4-lysozyme production would likely be minimal. When the final broth sample was examined under phase-contrast microscopy, it was observed that a substantial percentage of the cell population had lost the rod shape typical of intact healthy cells. Again, this observation was in line with that made with IGF-I, suggesting a low-level leakage of T4-lysozyme into the periplasmic compartment. That the broth viscosity appeared normal suggested the absence of significant cell lysis at this time. Similar results were obtained in another experiment (SRPVF5) in which arabinose was added earlier (1% arabinose added at 26 hrs). Like the VEGF fermentations, the respiration rate for the DNase culture declined late in the fermentation process at about 25-28 hrs post inoculation. Arabinose additions made at 24 hrs for induction of T4-lysozyme nucleic acid co-expression did not alter the on-set of the OUR loss. There were noticeable differences between the DNase process on the one hand, and the VEGF and IGF-I processes on the other. The cell lysis found in the harvested DNase broth that had been induced with a 1% arabinose addition made at 24 hrs was more severe than with the control without arabinose addition. When the induced culture was examined under the microscope, there appeared to be more weakened round-shaped cells and ghost cells that had lost their cellular contents than healthy intact cells.

Recovery of Refractile Particle from Harvested VEGF Broth:

The VEGF harvest broth showed some increase in broth viscosity after a single passage through the MICROFLUIDIZER® device, with transient visible lumpiness in the mechanically-disrupted broth. With an additional passage through the MICROFLUIDIZER® device, the broth viscosity was dramatically reduced. When mechanically-disrupted broths were centrifuged immediately after a single pass or two passes through the MICROFLUIDIZER® device, the resulting pellets appeared very spongy and tended to decant off with the supernatant if not carefully handled. Similar observations had been made with IGF-I control broth in the past.

Solids were recovered by centrifugation after three passes through the MICROFLUIDIZER® device. The size of the pellets recovered from broths co-expressing nucleic acid encoding T4-lysozyme and held for 2 hrs at 37° C. was similar to that obtained from control whole broth that is not mechanically disrupted and not passed through the MICROFLUIDIZER® device, indicating that, without being limited to any one theory, almost all of the solids were collected at the RCF of 4056×g and no differential sedimentation of VEGF aggregates from cell debris was achieved.

Qualitative assessment of product recovery efficiency was made by visual inspection of the intensity of the product band resolved by 10-20% TRICINE™ gel electrophoresis (see FIG. 16). Recovery of the VEGF aggregates appeared comparable across the various samples tested (including the lanes marked M3P/LE-1 hr (three passes plus 5 mM EDTA final concentration held at 37° C. for 1 hour), M3P/LE-2 hr (three passes plus 5 mM EDTA final concentration held at 37° C. for 2 hours), and M3P/LE-20 hr (three passes plus 5 mM EDTA final concentration held at 37° C. for 2 hours with room-temperature incubation for 18 hours). The gel profiles showed that a significant amount of the total proteins originally present in the whole broth co-sedimented with the VEGF aggregates. Without being limited to any one theory, it is believed that the refractile particles of VEGF might not have been as freed of contaminating *E. coli* proteins as the IGF-I refractile particles, and that the refractile particles of different products might differ in their densities or sizes, depending on the underlying phenomena that caused the aggregation of the proteins. Additionally, without limitation to any one theory, it is believed that the refractile particles might also vary in the manner in which they associated with other *E. coli* proteins and therefore cause different amounts of contaminating proteins to be entrapped in the product aggregates. Taken together, the results suggested that adjustments of the refractile particle recovery protocol within the guidelines set forth herein would maximize recovery of different refractile particles, depending on the polypeptide being recovered.

Recovery of Refractile Particles from Harvested DNase Broth:

During the processing of DNase broth for refractile particle recovery, the DNase pellets obtained by centrifugation after each of the three passes or one pass through the MICROFLUIDIZER® device appeared to be more compact than those of IGF-I or VEGF. The 10-20% TRICINE™ electrophoresis gel profile in FIG. 17 showed good recovery of DNase for the three process treatments. In fact, comparison of the lanes marked M3P (three passes plus 5 mM EDTA final concentration held at 37° C. for 2 hours), M1P (one pass plus 5 mM EDTA final concentration held at 37° C. for 2 hours), and M3P; no EDTA (three passes without EDTA) revealed that DNase requires only one pass through the MICROFLUIDIZER® device to be recovered in good quantity. The comparison also shows that it is preferred to add EDTA. These results illustrate the advantage of this invention in requiring less mechanical disruption of the cells so that less large-scale processing time is required than with conventional processing.

CONCLUSIONS

Co-expression of nucleic acid encoding a phage lysozyme (such as T4-lysozyme) with nucleic acid encoding a heterologous polypeptide, either from an ara-promoter-regulated gene inserted into the product plasmid or directed by a similar ara-promoter-phage-lysozyme-gene cassette in a second compatible plasmid, has been demonstrated to enhance recovery of heterologous polypeptide insoluble in the periplasm in accordance with the process of this invention. Under the conditions employed, the induction of expression of nucleic acid encoding phage lysozyme with arabinose addition did not negatively affect cell growth or product accumulation. Compared to HEW-lysozyme, the recovery of periplasmic refractile particles increased from approximately 50 to 90% with T4-lysozyme nucleic acid co-expression. The refractile particle recovery protocol established is both simple and scalable.

What is claimed is:

1. A replicable bacterial expression vector comprising a first nucleic acid encoding a mammalian polypeptide comprising a signal sequence for secretion into the periplasm, under control of a first inducible promoter, and a second nucleic acid encoding a phage lysozyme, in the absence of a signal sequence, under control of a second tightly-controlled inducible promoter, wherein said first and second promoters are different which can independently regulate the expression of said mammalian polypeptide and said phage lysozyme.

2. The replicable bacterial expression vector of claim 1 wherein the mammalian polypeptide is a human polypeptide.

3. The replicable bacterial expression vector of claim 2 wherein the human polypeptide is an insulin-like growth factor (IGF), DNAse, or vascular endothelial growth factor (VEGF).

4. The replicable bacterial expression vector of claim 3 wherein the human polypeptide is IGF-I.

5. The replicable bacterial expression vector of claim 4 wherein said first inducible promoter is an alkaline phosphatase promoter.

6. The replicable bacterial expression vector of claim 5 wherein said second tightly-controlled inducible promoter is an arabinose promoter.

7. The replicable bacterial expression vector of claim 6 wherein the the human polypeptide comprises a lamB signal sequence.

8. A bacterial host cell transformed with a replicable bacterial expression vector according to any one of claims 1 to 7.

9. The bacterial host cell of claim 8 which is a Gram-negative cell.

10. The bacterial host cell of claim 9 which is an *E. coli* cell.

11. The bacterial host cell of claim 10 comprising a mammalian polypeptide encoded by said bacterial expression vector accumulated in the periplasm thereof.

* * * * *

SEQUENCE LISTING

<160> NUMBER OF SEQ ID NOS: 3

<210> SEQ ID NO 1
<211> LENGTH: 1000
<212> TYPE: DNA
<213> ORGANISM: Homo sapiens

<400> SEQUENCE: 1

```
tcacgtaaaa agggtatcta gaggttgagg tgattttatg aaaaagaata            50
tcgcatttct tcttgcatct atgttcgttt tttctattgc tacaaatgcc           100
tatgcattga agatcgcagc cttcaacatc cagacatttg gggagaccaa           150
gatgtccaat gccaccctcg tcagctacat tgtgcagatc ctgagccgct           200
atgacatcgc cctggtccag gaggtcagag acagccacct gactgccgtg           250
gggaagctgc tggacaacct caatcaggat gcaccagaca cctatcacta           300
cgtggtcagt gagccactgg gacggaacag ctataaggag cgctacctgt           350
tcgtgtacag gcctgaccag gtgtctgcgg tggacagcta ctactacgat           400
gatggctgcg agccctgcgg gaacgacacc ttcaaccgag agccagccat           450
tgtcaggttc ttctcccggt tcacagaggt cagggagttt gccattgttc           500
ccctgcatgc ggccccgggg gaccgagtag ccgagatcga cgctctctat           550
gacgtctacc tggatgtcca agagaaatgg ggcttggagg acgtcatgtt           600
gatgggcgac ttcaatgcgg gctgcagcta tgtgagaccc tcccagtggt           650
catccatccg cctgtggaca agccccacct tccagtggct gatccccgac           700
agcgctgaca ccacagctac acccacgcac tgtgcctatg acaggatcgt           750
ggttgcaggg atgctgctcc gaggcgccgt tgttcccgac tcggctcttc           800
```

| | |
|---|---:|
| cctttaactt ccaggctgcc tatggcctga gtgaccaact ggcccaagcc | 850 |
| atcagtgacc actatccagt ggaggtgatg ctgaagtaag ctaattctca | 900 |
| tgtttgacag cttatcatcg ataagcttta atgcggtagt ttatcacagt | 950 |
| taaattgcta acgcagtcag gcaccgtgta tgaaatctaa caatgcgctc | 1000 |

<210> SEQ ID NO 2
<211> LENGTH: 1000
<212> TYPE: DNA
<213> ORGANISM: Homo sapiens

<400> SEQUENCE: 2

| | |
|---|---:|
| gagcgcattg ttagatttca tacacggtgc ctgactgcgt tagcaattta | 50 |
| actgtgataa actaccgcat taaagcttat cgatgataag ctgtcaaaca | 100 |
| tgagaattag cttacttcag catcacctcc actggatagt ggtcactgat | 150 |
| ggcttgggcc agttggtcac tcaggccata ggcagcctgg aagttaaagg | 200 |
| gaagagccga gtcgggaaca acggcgcctc ggagcagcat ccctgcaacc | 250 |
| acgatcctgt cataggcaca gtgcgtgggt gtagctgtgg tgtcagcgct | 300 |
| gtcggggatc agccactgga aggtggggct tgtccacagg cggatggatg | 350 |
| accactggga gggtctcaca tagctgcagc ccgcattgaa gtcgcccatc | 400 |
| aacatgacgt cctccaagcc ccatttctct tggacatcca ggtagacgtc | 450 |
| atagagagcg tcgatctcgg ctactcggtc ccccggggcc gcatgcaggg | 500 |
| gaacaatggc aaactccctg acctctgtga accgggagaa gaacctgaca | 550 |
| atggctggct ctcggttgaa ggtgtcgttc ccgcagggct cgcagccatc | 600 |
| atcgtagtag tagctgtcca ccgcagacac ctggtcaggc ctgtacacga | 650 |
| acaggtagcg ctccttatag ctgttccgtc ccagtggctc actgaccacg | 700 |
| tagtgatagg tgtctggtgc atcctgattg aggttgtcca gcagcttccc | 750 |
| cacggcagtc aggtggctgt ctctgacctc ctggaccagg gcgatgtcat | 800 |
| agcggctcag gatctgcaca atgtagctga cgagggtggc attggacatc | 850 |
| ttggtctccc caaatgtctg gatgttgaag gctgcgatct tcaatgcata | 900 |
| ggcatttgta gcaatagaaa aaacgaacat agatgcaaga agaaatgcga | 950 |
| tattctttt cataaaatca cctcaacctc tagatacccct ttttacgtga | 1000 |

<210> SEQ ID NO 3
<211> LENGTH: 283
<212> TYPE: PRT
<213> ORGANISM: Homo sapiens

<400> SEQUENCE: 3

Met Lys Lys Asn Ile Ala Phe Leu Leu Ala Ser Met Phe Val Phe
1               5                   10                  15

Ser Ile Ala Thr Asn Ala Tyr Ala Leu Lys Ile Ala Ala Phe Asn
            20                  25                  30

Ile Gln Thr Phe Gly Glu Thr Lys Met Ser Asn Ala Thr Leu Val
            35                  40                  45

Ser Tyr Ile Val Gln Ile Leu Ser Arg Tyr Asp Ile Ala Leu Val
            50                  55                  60

Gln Glu Val Arg Asp Ser His Leu Thr Ala Val Gly Lys Leu Leu
        65                  70                  75

-continued

```
Asp Asn Leu Asn Gln Asp Ala Pro Asp Thr Tyr His Tyr Val Val
            80                  85                  90

Ser Glu Pro Leu Gly Arg Asn Ser Tyr Lys Glu Arg Tyr Leu Phe
            95                  100                 105

Val Tyr Arg Pro Asp Gln Val Ser Ala Val Asp Ser Tyr Tyr Tyr
            110                 115                 120

Asp Asp Gly Cys Glu Pro Cys Gly Asn Asp Thr Phe Asn Arg Glu
            125                 130                 135

Pro Ala Ile Val Arg Phe Phe Ser Arg Phe Thr Glu Val Arg Glu
            140                 145                 150

Phe Ala Ile Val Pro Leu His Ala Ala Pro Gly Asp Arg Val Ala
            155                 160                 165

Glu Ile Asp Ala Leu Tyr Asp Val Tyr Leu Asp Val Gln Glu Lys
            170                 175                 180

Trp Gly Leu Glu Asp Val Met Leu Met Gly Asp Phe Asn Ala Gly
            185                 190                 195

Cys Ser Tyr Val Arg Pro Ser Gln Trp Ser Ser Ile Arg Leu Trp
            200                 205                 210

Thr Ser Pro Thr Phe Gln Trp Leu Ile Pro Asp Ser Ala Asp Thr
            215                 220                 225

Thr Ala Thr Pro Thr His Cys Ala Tyr Asp Arg Ile Val Val Ala
            230                 235                 240

Gly Met Leu Leu Arg Gly Ala Val Val Pro Asp Ser Ala Leu Pro
            245                 250                 255

Phe Asn Phe Gln Ala Ala Tyr Gly Leu Ser Asp Gln Leu Ala Gln
            260                 265                 270

Ala Ile Ser Asp His Tyr Pro Val Glu Val Met Leu Lys
            275                 280
```